(12) United States Patent
Sullivan

(10) Patent No.: US 12,708,306 B2
(45) Date of Patent: Aug. 18, 2026

(54) DETECTION OF CHRONIC ELECTRODE LEADS OFF

(71) Applicant: West Affum Holdings DAC, Dublin (IE)

(72) Inventor: Joseph L. Sullivan, Kirkland, WA (US)

(73) Assignee: West Affum Holdings DAC, Dublin (IE)

( * ) Notice: Subject to any disclaimer, the term of this patent is extended or adjusted under 35 U.S.C. 154(b) by 665 days.

(21) Appl. No.: 17/546,949

(22) Filed: Dec. 9, 2021

(65) Prior Publication Data

US 2022/0401003 A1 Dec. 22, 2022

Related U.S. Application Data

(60) Provisional application No. 63/213,658, filed on Jun. 22, 2021.

(51) Int. Cl.

| | |
|---|---|
| ***A61B 5/276*** | (2021.01) |
| ***A61B 5/00*** | (2006.01) |
| ***A61B 5/024*** | (2006.01) |
| ***A61B 5/256*** | (2021.01) |
| ***A61B 5/257*** | (2021.01) |

(52) U.S. Cl.

CPC .......... *A61B 5/276* (2021.01); *A61B 5/02438* (2013.01); *A61B 5/256* (2021.01); *A61B 5/257* (2021.01); *A61B 5/7264* (2013.01); *A61B 5/742* (2013.01); *A61B 5/746* (2013.01)

(58) Field of Classification Search

CPC ..... A61B 5/276; A61B 5/02438; A61B 5/256; A61B 5/257; A61B 5/7264; A61B 5/742; A61B 5/746

See application file for complete search history.

(56) References Cited

U.S. PATENT DOCUMENTS

| | | | |
|---|---|---|---|
| 3,724,355 | A | 4/1973 | Busch et al. |
| 3,724,455 | A | 4/1973 | Unger |
| 4,583,524 | A | 4/1986 | Hutchins |

(Continued)

FOREIGN PATENT DOCUMENTS

| | | | | |
|---|---|---|---|---|
| DE | 102005060985 A1 | | 6/2007 | |
| EP | 1114613 A2 | * | 7/2001 | ......... A61B 5/04845 |

(Continued)

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

(Continued)

*Primary Examiner* — Amanda L Steinberg
*Assistant Examiner* — Laura Hodge
(74) *Attorney, Agent, or Firm* — Seed Intellectual Property Law Group LLP

(57) ABSTRACT

Technologies and implementations for a wearable healthcare system including one or more electrodes, which may detect and determine smart leads off conditions of the one or more electrodes. The wearable healthcare system may include a leads off monitor module, which may be configured to learn when and when not to cause a leads off alert.

28 Claims, 8 Drawing Sheets

(56) References Cited

U.S. PATENT DOCUMENTS 4,619,265 A 10/1986 Morgan et al.
4,666,432 A 5/1987 McNeish et al.
4,698,848 A 10/1987 Buckley
4,928,690 A 5/1990 Heilman et al.
4,955,381 A 9/1990 Way et al.
5,078,134 A 1/1992 Heilman et al.
5,228,449 A 7/1993 Christ et al.
5,348,008 A 9/1994 Bornn et al.
5,353,793 A 10/1994 Bornn
RE34,800 E 11/1994 Hutchins
5,394,892 A 3/1995 Kenny
5,405,362 A 4/1995 Kramer et al.
5,429,593 A 7/1995 Matory
5,474,574 A 12/1995 Payne et al.
5,618,208 A 4/1997 Crouse et al.
5,662,690 A 9/1997 Cole et al.
5,708,978 A 1/1998 Johnsrud
5,741,306 A 4/1998 Glegyak et al.
5,782,878 A 7/1998 Morgan et al.
5,792,204 A 8/1998 Snell
5,902,249 A 5/1999 Lyster
5,913,685 A 6/1999 Hutchins
5,944,669 A 8/1999 Kaib
6,047,203 A 4/2000 Sackner et al.
6,065,154 A 5/2000 Hulings et al.
6,108,197 A 8/2000 Janik
6,148,233 A 11/2000 Owen et al.
6,201,992 B1 3/2001 Freeman
6,263,238 B1 7/2001 Brewer et al.
6,280,461 B1 8/2001 Glegyak et al.
6,287,328 B1 9/2001 Snyder et al.
6,304,780 B1 10/2001 Owen et al.
6,319,011 B1 11/2001 Motti et al.
6,334,070 B1 12/2001 Nova et al.
6,356,785 B1 3/2002 Snyder
6,427,083 B1 7/2002 Owen et al.
6,437,083 B1 8/2002 Brack et al.
6,450,942 B1 9/2002 Lapanashvili et al.
6,529,875 B1 3/2003 Nakajima
6,546,285 B1 4/2003 Owen et al.
6,671,545 B2 12/2003 Fincke
6,681,003 B2 1/2004 Linder et al.
6,762,917 B1 7/2004 Verbiest et al.
7,065,401 B2 6/2006 Worden
7,099,715 B2 8/2006 Korzinov et al.
7,212,850 B2 5/2007 Prystowsky et al.
7,559,902 B2 7/2009 Ting et al.
7,587,237 B2 9/2009 Korzinov et al.
7,753,759 B2 7/2010 Pintor et al.
7,865,238 B2 1/2011 Brink
7,870,761 B2 1/2011 Valentine et al.
7,907,996 B2 3/2011 Prystowsky et al.
7,941,207 B2 5/2011 Korzinov
7,974,689 B2 7/2011 Volpe et al.
8,135,462 B2 3/2012 Owen et al.
8,140,154 B2 3/2012 Donnelly et al.
8,369,944 B2 2/2013 Macho et al.
8,527,028 B2 9/2013 Kurzweil et al.
8,548,557 B2 10/2013 Garstka et al.
8,560,044 B2 10/2013 Kurzweil et al.
8,615,295 B2 12/2013 Savage et al.
8,644,925 B2 2/2014 Volpe et al.
8,676,313 B2 3/2014 Volpe et al.
8,706,255 B2 4/2014 Phillips et al.
8,742,349 B2 6/2014 Urbon et al.
8,897,860 B2 11/2014 Volpe et al.
8,904,214 B2 12/2014 Volpe et al.
8,965,500 B2 2/2015 Macho et al.
9,008,801 B2 4/2015 Kaib et al.
9,084,583 B2 7/2015 Mazar et al.
9,089,685 B2 7/2015 Sullivan et al.
9,119,547 B2 9/2015 Cazares et al.
9,131,901 B2 9/2015 Volpe et al.
9,132,267 B2 9/2015 Kaib
9,237,858 B2 1/2016 Krusor et al.
9,265,432 B2 2/2016 Warren et al.
9,345,898 B2 5/2016 Piha et al.
9,408,548 B2 8/2016 Volpe et al.
9,445,719 B2 9/2016 Libbus et al.
9,454,219 B2 9/2016 Volpe et al.
9,579,020 B2 2/2017 Libbus et al.
9,592,403 B2 3/2017 Sullivan
9,598,799 B2 3/2017 Shoshani et al.
9,675,804 B2 6/2017 Whiting et al.
9,724,008 B2 8/2017 Sullivan et al.
9,878,171 B2 1/2018 Kaib
9,895,105 B2 2/2018 Romem
9,901,741 B2 2/2018 Chapman et al.
RE46,926 E 7/2018 Bly et al.
10,016,613 B2 7/2018 Kavounas
10,076,656 B2 9/2018 Dar et al.
10,192,387 B2 1/2019 Brinig et al.
10,307,133 B2 6/2019 Kaib
10,463,867 B2 11/2019 Kaib et al.
10,589,110 B2 3/2020 Oskin et al.
10,599,814 B2 3/2020 Landrum et al.
2002/0181680 A1 12/2002 Linder et al.
2003/0158593 A1 8/2003 Heilman et al.
2005/0107833 A1 5/2005 Freeman et al.
2005/0107834 A1 5/2005 Freeman et al.
2006/0173499 A1 8/2006 Hampton et al.
2008/0312709 A1 12/2008 Volpe et al.
2009/0005827 A1 1/2009 Weintraub et al.
2010/0007413 A1 1/2010 Herleikson
2010/0298899 A1 11/2010 Donnelly et al.
2011/0022105 A9 1/2011 Owen et al.
2011/0288604 A1 11/2011 Kaib et al.
2011/0288605 A1 11/2011 Kaib et al.
2012/0112903 A1 5/2012 Kaib et al.
2012/0144551 A1 6/2012 Guldalian
2012/0150008 A1 6/2012 Kaib et al.
2012/0158075 A1 6/2012 Kaib et al.
2012/0191476 A1 7/2012 Reid et al.
2012/0265265 A1 10/2012 Razavi et al.
2012/0283794 A1 11/2012 Kaib et al.
2012/0293323 A1 11/2012 Kaib et al.
2012/0302860 A1 11/2012 Volpe et al.
2012/0310315 A1 12/2012 Savage et al.
2013/0085538 A1 4/2013 Volpe et al.
2013/0144355 A1 6/2013 Macho et al.
2013/0231711 A1 9/2013 Kaib
2013/0245388 A1 9/2013 Rafferty et al.
2013/0274565 A1 10/2013 Langer et al.
2013/0317852 A1 11/2013 Worrell et al.
2013/0325078 A1 12/2013 Whiting et al.
2014/0012144 A1 1/2014 Crone
2014/0025131 A1 1/2014 Sullivan et al.
2014/0046391 A1 2/2014 Cowan et al.
2014/0070957 A1 3/2014 Longinotti-Buitoni et al.
2014/0163663 A1 6/2014 Poddar et al.
2014/0247058 A1* 9/2014 Mortara ................. A61B 5/276 324/601
2014/0296935 A1* 10/2014 Ferree .................. A61N 1/3603 607/46
2014/0324112 A1 10/2014 Macho et al.
2014/0378812 A1 12/2014 Saroka et al.
2015/0039053 A1 2/2015 Kaib et al.
2015/0161554 A1 6/2015 Sweeney et al.
2015/0297135 A1 10/2015 Shoshani et al.
2015/0328472 A1 11/2015 Sullivan et al.
2016/0004831 A1 1/2016 Carlson et al.
2016/0076175 A1 3/2016 Rock et al.
2016/0076176 A1 3/2016 Rock et al.
2016/0082277 A1 3/2016 Foshee, Jr. et al.
2016/0113581 A1 4/2016 Amir et al.
2016/0256104 A1 9/2016 Romem et al.
2016/0283900 A1 9/2016 Johnson et al.
2017/0014073 A1 1/2017 Shoshani et al.
2017/0027469 A1 2/2017 Amir et al.
2017/0036066 A1 2/2017 Chahine
2017/0040758 A1 2/2017 Amir et al.
2017/0056650 A1* 3/2017 Cohen .................. A61N 1/3603
2017/0086699 A1* 3/2017 Shirai .................... A61B 5/282
2017/0162840 A1 6/2017 Pendry

(56) References Cited

U.S. PATENT DOCUMENTS

| | | | | |
|---|---|---|---|---|
| 2017/0319862 | A1 | 11/2017 | Foshee, Jr. et al. | |
| 2017/0367591 | A1 | 12/2017 | Jorgensen | |
| 2018/0116537 | A1 | 5/2018 | Sullivan et al. | |
| 2018/0117299 | A1 | 5/2018 | Gustavson et al. | |
| 2018/0168508 | A1 * | 6/2018 | Biel | A61B 5/282 |
| 2018/0184933 | A1 | 7/2018 | Sullivan et al. | |
| 2018/0185662 | A1 | 7/2018 | Foshee, Jr. et al. | |
| 2018/0243578 | A1 | 8/2018 | Volosin | |
| 2018/0361165 | A1 | 12/2018 | Jaax et al. | |
| 2019/0030351 | A1 | 1/2019 | Sullivan et al. | |
| 2019/0030352 | A1 | 1/2019 | Sullivan et al. | |
| 2019/0076666 | A1 | 3/2019 | Medema | |
| 2019/0116896 | A1 | 4/2019 | Armour et al. | |
| 2019/0321650 | A1 | 10/2019 | Raymond et al. | |
| 2021/0052227 | A1 | 2/2021 | Engman et al. | |

FOREIGN PATENT DOCUMENTS

| | | | |
|---|---|---|---|
| EP | 2305110 | A1 | 4/2011 |
| EP | 3380189 | B1 | 10/2018 |
| JP | 4320257 | B2 | 8/2009 |
| JP | 2014526282 | A | 10/2014 |
| JP | 5963767 | B2 | 8/2016 |
| WO | 1998039061 | A2 | 9/1998 |
| WO | 2011/146448 | A1 | 11/2011 |
| WO | 2012064604 | A1 | 5/2012 |
| WO | 2012/151160 | A1 | 11/2012 |
| WO | 2015/056262 | A1 | 4/2015 |

OTHER PUBLICATIONS

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

Metting Van Rijn, A. C., Peper A., & Grimbergen, C. A., High-Quality Recording of Bioelectric Events Part 1: Interference Reduction, Theory and Practice, Review, Medical & Biological Engineering & Computing, Sep. 1990, pp. 389-397, IFMBE.

Pagan-Carlo, et al., "Encircling Overlapping Multipulse Shock Waveforms for Transthoracic Defibrillation," JACC Journals, Dec. 1998, vol. 32 Issue 7, p. 2065-2071.

Zoll, LifeVest, Proven protection from Sudden Cardiac Death, 2017, 4 pages. Pittsburgh PA, USA.

International Search Report and Written Opinion for PCT Application No. PCT/US2015/051726, dated May 20, 2016, European Patent Office, Rijswijk, 11 pages.

* cited by examiner

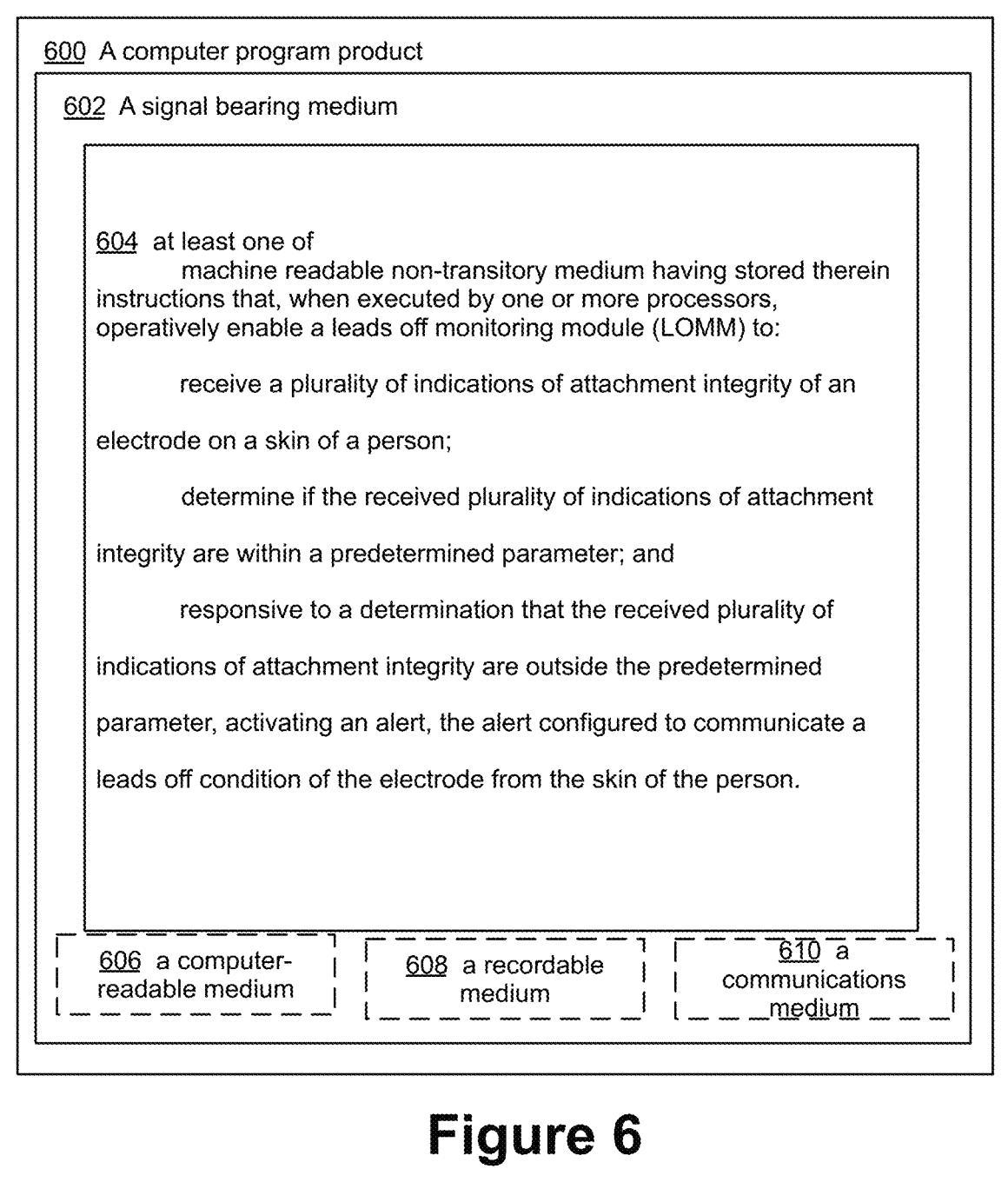

600 A computer program product

602 A signal bearing medium 604 at least one of
machine readable non-transitory medium having stored therein instructions that, when executed by one or more processors, operatively enable a leads off monitoring module (LOMM) to:

receive a plurality of indications of attachment integrity of an electrode on a skin of a person;

determine if the received plurality of indications of attachment integrity are within a predetermined parameter; and responsive to a determination that the received plurality of indications of attachment integrity are outside the predetermined parameter, activating an alert, the alert configured to communicate a leads off condition of the electrode from the skin of the person.

606 a computer-readable medium 608 a recordable medium 610 a communications medium

Figure 6

DETECTION OF CHRONIC ELECTRODE LEADS OFF

RELATED APPLICATION

This application claims benefit of priority to U.S. Provisional Patent Application Ser. No. 63/213,658, filed on Jun. 22, 2021, titled DETECTION OF CHRONIC ELECTRODE LEADS OFF, which is incorporated herein by reference in its entirety for all purposes.

INFORMATION

Unless otherwise indicated herein, the approaches described in this section are not prior art to the claims in this application and are not admitted to be prior art by inclusion in this section.

Technology has contributed to improvements in healthcare. Some examples include healthcare related devices that may be capable of determining various health related information about a person. For example, a healthcare device may be capable of determining health related information of an electrical activity of a person. The electrical activities of the person may include various electrical activities of various organs such as, but not limited to, brain activities, heart activities, skin moisture, gastrointestinal tract activities, breathing activities, etc.

For example, a healthcare device may be configured to monitor the electrical activities of the heart and/or treat potential health related issues with the heart. An example of a medical device for monitoring the electrical activities of the heart may be a healthcare device configured to monitor the heart such as, but not limited to, an electrocardiogram (ECG) device. The ECG device may include one or more electrodes communicatively coupled with the ECG device. The electrodes may be adhesively attached to a skin of the person proximate to the person's heart. The electrode may be configured to receive the electrical signals from the person's heart activity and communicate the electrical signals to the ECG device to processed.

Because the electrode may be configured to adhesively contact with the skin to receive the electrical signals, changes in the contact between the skin and the electrode may affect the received electrical signal (ECG) signal. In one example, if the electrode no longer contacts the skin, the ECG signals may be negatively affected (i.e., the electrode may be no longer receive the ECG signals). In another example, if the electrode contact with the skin is reduced (e.g., falling off the skin), the ECG signal may be negatively affected as well. The changes in the contact between the skin and the electrode may occur due to movement of the person (i.e., movement of the skin).

All subject matter discussed in this section of this document is not necessarily prior art and may not be presumed to be prior art simply because it is presented in this section. Plus, any reference to any prior art in this description is not and should not be taken as an acknowledgement or any form of suggestion that such prior art forms parts of the common general knowledge in any art in any country. Along these lines, any recognition of problems in the prior art are discussed in this section or associated with such subject matter should not be treated as prior art, unless expressly stated to be prior art. Rather, the discussion of any subject matter in this section should be treated as part of the approach taken towards the particular problem by the inventor(s). This approach in and of itself may also be inventive. Accordingly, the foregoing summary is illustrative only and not intended to be in any way limiting. In addition to the illustrative aspects, embodiments, and features described above, further aspects, embodiments, and features will become apparent by reference to the drawings and the following detailed description.

SUMMARY

Described herein are various illustrative electrical signal monitoring medical systems and methods that may include a leads off monitor module (LOMM). Example systems may include an electrode, which may be attachable to a skin of a person and configured to receive electrical signals. Example systems may include LOMMs that may be configured to receive a number of indications of attachment integrity of the electrode on the skin. Some example LOMMs may be configured to determine if the received number of indications of attachment integrity are within a predetermined parameter. Responsive to a determination that the received number of indications are outside the predetermined parameter, some example LOMMs may be configured to activate an alert. The alert may be configured to communicate a leads off condition of the electrode from the skin.

The foregoing summary is illustrative only and not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIG. 6 illustrates an example computer program product, arranged in accordance with at least some embodiments described herein.

DETAILED DESCRIPTION

Figure 1:
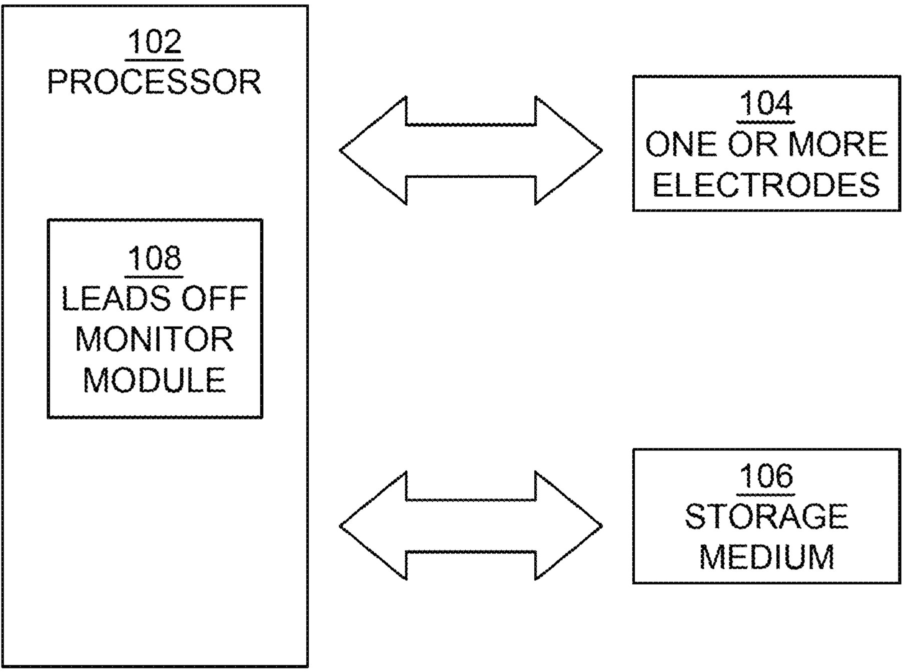
FIG. 1 illustrates a block diagram of a system for intelligent alerts for leads off conditions for an electrode of a medical device, in accordance with various embodiments.

The following description sets forth various examples along with specific details to provide a thorough understanding of claimed subject matter. It will be understood by those skilled in the art after review and understanding of the present disclosure, however, that claimed subject matter may be practiced without some or more of the specific details disclosed herein. Further, in some circumstances, well-known methods, procedures, systems, components and/or circuits have not been described in detail in order to avoid unnecessarily obscuring claimed subject matter.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

This disclosure is drawn, inter alia, to methods, apparatus, and systems related to a medical device having a smart leads off monitoring module. Accordingly, the medical device having a smart leads off monitoring module, which may facilitate intelligent alerts for leads off conditions for an electrode of the medical device.

In the present disclosure, a medical device may include a medical device that may be configured to facilitate monitoring of electrical signals such as, but not limited to, monitoring of electrical signals from a heart of a person. For example, the medical device may be configured to monitor and treat potential issues with the heart (i.e., the person may have a health condition, where the electrical control system of the heart may malfunction causing the heart to beat irregularly or not at all). In some examples, these types of medical devices may include a defibrillator device. In some examples, these types of medical devices may be wearable such as, but not limited to, a wearable medical device (WMD). An example of a WMD, which may be configured to monitor and treat potential issues with the heart, may include a wearable cardioverter defibrillator (WCD). In the present disclosure, for the purposes of ease of understanding the various embodiments of the claimed subject matter, references may be made to a WCD, where the WCD may include various examples of a smart leads off monitoring modules. However, in accordance with various embodiments, a wide variety of healthcare/medical devices, which may be utilized to monitor various electrical activities of various organs, may be included. Accordingly, the claimed subject matter is not limited in this respect.

For example, it should be appreciated that in some embodiments, the medical device may be a wide variety of medical devices configured to utilize electrodes for various monitoring of electrical activities. Some examples of medical devices may include cardiac event monitors, Holter monitors, mobile cardiac telemetry (MCT) devices, brain activity monitors, etc. Accordingly, claimed subject matter is not limited in this respect.

For ease of understanding the subject matter of the disclosure, an example of a healthcare/medical device utilized to monitor and/or treat heart related conditions may be described. As part of the description of a healthcare/medical device related the activities of the heart, briefly, some issues with the rate of the heartbeat may be generally referred to as an arrhythmia. Arrhythmia may be caused by many factors, but in general, an arrhythmia may be caused by a malfunction in the electrical control system of the heart. Some types of arrhythmias may result in inadequate blood flow resulting in reduction or lack of the amount of blood pumped to the various parts of the body. For example, issues with the sinoatrial (SA) node may lead to an arrhythmia of some kind. Some arrhythmias may lead to a condition known as sudden cardiac arrest (SCA). In an SCA condition, the heart may fail to pump blood effectively, and as a result, death may occur.

An example type of arrhythmia, which may be associated with SCA, may be a condition known as ventricular fibrillation (VF). VF may be a condition where a ventricle or ventricles, which make up the heart to facilitate the pumping of blood, may make uncoordinated movements instead of steady rhythmic movements. In the VF condition, the heart may not pump adequate amounts of blood or may not pump blood at all, which may eventually lead to death. Another type of arrhythmia, which may be associated with SCA, may be a condition known as ventricular tachycardia (VT).

Turning back to the medical device configured to be utilized to monitor and/or provide therapy to the heart, the medical device may be capable of monitoring the electrical signals of the heart and if necessary, administer therapy to the heart in the form of an electric shock. The medical device may monitor the electrical signals and provide the electric shock to the heart externally (i.e., through the surface of a body) via components commonly known as electrodes, where some of the electrodes may be monitoring electrodes and some of the electrodes may be therapy electrodes. The medical device may be in the form of a cardioverter defibrillator. The medical device may be included in a support structure configured to be worn by the person. In this example, the medical device may help facilitate monitoring the electrical activities of the heart and provide the electric shock to the heart in the VF condition. As a result, the medical device may help prevent Sudden Cardiac Death (SCD).

Since the monitoring of the electrical signals from the person's heart may be received through the surface of the body of the person (i.e., the skin), the electrodes may be configured to be attachable to the skin. The attachment may be provided by conductive adhesives to facilitate the attachment of the electrodes to the skin. In addition to the conductive adhesive, the attachment of the electrodes to the skin may be facilitated by the support structure, which may include the electrodes. The electrical signals may be received by the electrodes via a contact interface between the monitoring electrodes and the skin. The contact interface may affect the integrity of electrical signals received by the monitoring electrodes. The integrity of electrical signals received by the monitoring electrodes may affect the processing of the electrical signals by the medical device.

Some examples of conductive adhesives may include some form of moisturizer, electrolytic gel, and/or various conductive fluid/moisture material. The conductive adhesive may facilitate attachment of the electrodes at the contact interface between the electrodes and the skin and maintain and/or promote the integrity of the electrical signals received and/or provided by the electrodes.

Similar to the monitoring electrodes, a contact interface between the therapy electrodes and the skin may affect the electrical shock that may be provided to the heart. The electrical shock provided to the heart may be predetermined to provide enough of an electrical shock to facilitate therapy of the heart. However, if the contact interface is negatively affected, the provided shock may not be the predetermined amount, which may negatively affect the therapy.

Before turning the figures, a non-limiting example scenario may be described. In the non-limiting example scenario, a person may have a heart condition, where the person may utilize a wearable medical device (WMD). The WMD may be configured to facilitate monitoring and treatment of a heart condition of the person such as, but not limited to, a wearable cardioverter defibrillator (WCD). The WCD may include a support structure configured to be worn by the person such as, but not limited to, a garment (e.g., a vest). Included in the support structure of the WCD, a WCD monitor may include various components to facilitate the functionality of the WCD. A number of electrodes, monitoring electrodes and therapy electrodes, may be communicatively coupled with the WCD monitor.

The monitoring electrodes may be disposed on a skin of the person proximate to the heart of the person. The monitoring electrodes may be configured to detect and receive electrocardiogram (ECG) signals from the heart of the person. Likewise, the therapy electrodes may be disposed on the skin of the person proximate to the heart of the person. The therapy electrodes may be configured to provide an electrical shock to the heart as part of the therapy for a condition of the heart. Since the monitoring electrodes and the therapy electrodes may be disposed on the skin to receive and/or deliver electrical signals, a contact interface between the electrodes and the skin may affect the receipt and/or delivery of the electrical signals as described above.

A monitoring electrode may include a sensor that may be disposed at the contact interface. The sensor may be configured to detect the electrical signals of the heart (e.g., ECG signals) of the person. A therapy electrode may include a shock pad disposed at the contact interface. The shock pad may be configured to deliver an electric shock to the heart of the person.

Since the sensor and the shock pads may be reliant upon receipt and/or transmission of electrical signals, the contact interface between the sensor and/or the shock pad may affect the receipt and/or transmission of electrical signals. For example, if the contact interface becomes low or poor, the integrity of the electrical signals received and/or transmitted by medical device via the electrode may be negatively affected. In turn, the contact interface may be affected by the attachment of the electrode (i.e., attachment integrity of the electrode on the skin). Accordingly, when the attachment integrity becomes low or poor, the medical device may be configured to provide an alert.

For the purposes of describing present disclosure, a single electrode may be described. However, it should be appreciated that one or more electrodes may be utilized by a healthcare/medical devices. Accordingly, the claimed subject matter is not limited in this respect. Accordingly, in this non-limiting example, a single monitoring electrode (electrode) may be adhesively attached to the skin of the person. The electrode may be configured to receive electrical signals (e.g., ECG signals). As the person goes about their daily activities, the contact interface between the electrode and the skin may change over a period of time. For example, as the person moves, the electrode may begin to detach from the skin, which may cause the LOMM to receive the indication that the electrode attachment may be poor (i.e., the electrode attachment integrity may be outside the tolerance prescribed by a healthcare professional and/or the medical device manufacturer). The received indications may cause one or more alarms to be activated (e.g., sound and/or visual indication). However, prior to activating one or more alerts regarding the electrode, the LOMM may determine if the indications may be false indications (i.e., false alarms), in accordance with various embodiments. As will be described, the LOMM may include machine learning capabilities, and accordingly, the LOMM may determine whether a received indication of an electrode attachment may cause or not cause an alert.

Continuing with the non-limiting scenario, the person may be wearing a WCD, which may include a leads off monitor module (LOMM). The LOMM may be configured to monitor the contact interface between an electrode and the skin of the person. The LOMM may determine whether to activate an alarm regarding the contact interface (i.e., leads off condition of the electrode). For example, the LOMM may be configured to receive a number of indications of attachment integrity of the electrode on the skin. The indications of the attachment integrity may be triggered by some form of indications that the contact interface may be poor (i.e., the electrode may have started coming off the skin or detached from the skin). The LOMM may determine if the received indications of the attachment integrity are within a predetermined parameter. Responsive to a determination that the number of indications of attachment integrity are outside the predetermined parameter, the LOMM may activate an alert. The alert configured to communicate a leads off condition of the electrode from the skin. However, if the LOMM determines that the received indication are within the predetermined parameter, the LOMM may not activate an alert and continue functioning as normal.

In one example, the number of indications may be received over a period of time. In this example, the LOMM may be configured to, responsive to a determination that the number of indications of attachment integrity over a period of time is outside the predetermined parameter, the LOMM may be configured to activate an alert.

In another example, the LOMM may be configured to inject a low-level current through the person and measure a voltage at the contact interface of the electrode. In this example, if the voltage measured at the contact interface of the electrode exceeds a threshold voltage (e.g., a 1 volt threshold may be set, which may correspond to a 100 k electrode impedance), the LOMM may cause the alarm to be provided. However, if the impedance does not exceed the threshold voltage, the LOMM may be configured to not provide the alarm. An example of utilizing impedance to detect a leads off condition may be found in US Patent Application Publication No. US20210052227A1; titled ALERT PRESENTATION BASED ON ANCILLARY DEVICE CONDITIONS, which is incorporated herein in its entirety for all purposes. It should be mentioned that in some embodiments, various methods may be utilized to determine a frequency of received indications, a rate of received indications, duty cycle of a medical device may be utilized, a period of occurrences may be utilized, etc. Accordingly, the claimed subject matter is not limited in these respects.

Continuing with the above example, as the person moves around such as, but not limited to, sitting, lying down, walking, running, etc., the electrode may periodically begin to come off the skin. However, the electrode may have only slightly come off the skin (i.e., the integrity of the electrical signals may still be within tolerance for the WCD). The LOMM may determine that the number of attachment integrity received are within the predetermined parameter (i.e., within the tolerance of the WCD), and accordingly, the LOMM may not activate an alert facilitating avoidance of a false alarm. Conversely, the LOMM may determine that the number of attachment integrity received are outside the predetermined parameter (i.e., outside the tolerance of the medical device), and accordingly, the LOMM may activate an alert. Responsive to the alert, the person may utilize some form of correction (i.e., adjust the electrode and/or the support structure to place the attachment integrity within the tolerance).

As described, the LOMM may be configured to determine that the number of attachment integrity received are outside the predetermined parameter for the period of time. In further detail, as the person moves, the electrode may have slightly lifted off the skin causing the attachment integrity to be outside the tolerance. However, the electrode may settle back onto the skin as the person stops moving. The LOMM may be configured to determine if the attachment integrity is outside the tolerance for a period of time to help facilitate reduction of alerts that may not be necessary. For example, the LOMM may be configured to determine if the attachment integrity of the electrode is outside the tolerance by approximately 25% for a period of 10 minutes. If it is determined that the attachment integrity of the electrode is outside the tolerance by approximately 25% for 10 minutes, the LOMM may cause an alert. Continuing with this example, the tolerance percentage and time period may be a wide range of percentages and time periods such as, but not limited to, 10% to 100% (i.e., approximately 10% lifted off to approximately completely off the skin) and approximately 1 minute to approximately 60 minutes. The predetermined parameters may be set by a number variety of manners such as, but not limited to, the WCD manufacturer, a healthcare professional, etc. Accordingly, the claimed subject matter is not limited in these respects.

As mentioned previously, references may be made to a single electrode. However, the claimed subject matter may include more than one electrode. For example, a monitoring medical system may include a number of electrodes (e.g., monitoring and/or therapy electrodes). In this example, a predetermined parameter may include any combination of described leads off indications with a determination of a number of electrodes that may cause a number of indications of attachment integrity to be received by the LOMM (e.g., various leads off conditions described herein). In one example, the determination of the number of electrodes may include 2 electrodes having leads off indications out of 5 total number of electrodes. In another example, the number of may include 3 electrodes having leads off indications out of 12 total number of electrodes. In a further example, the predetermined parameter may include a combination of number of electrodes having leads off indications and duration of the leads off. For example, the predetermined parameter may include conditions where if one electrode has a leads off condition, the predetermined parameter may be determined to be outside after a period of time (e.g., 15 minutes). However, if two or more electrodes has leads of condition, the predetermined parameter may be determined to be outside after another period of time (e.g., 1 minute. In further examples, the combination of times and number of leads off conditions may be based, at least in part, on each other. For example, 1 leads off may be 15 minutes, 2 leads may require 5 minutes, 3 leads off may be 2, and so forth.

The determination of a number of electrodes having leads off conditions may be a wide variety of numbers based, at least in part, on the device tolerance, manufacturer specifications, healthcare personnel recommendations, etc. Accordingly, the claimed subject matter is not limited in this respect. Prior to continuing with the description, it should be mentioned that in various embodiments, the predetermined parameter may include the number of electrode parameter and/or various parameters described herein and any combination thereof (e.g., number electrodes indicating leads off conditions and/or time).

In some examples, the LOMM may be configured to determine that the above percentages and time periods may be indicative of some form on/off condition as the person moves (e.g., walking, running, etc.) while wearing the WCD. The LOMM may receive an indication of periodic changes in the attachment integrity (i.e., on/off conditions). The periodic changes in attachment integrity received by the LOMM may continue to be within the predetermined parameters, and accordingly, the LOMM may not cause an alert. However, if the LOMM determines that the periodic changes in the attachment integrity are outside the predetermined parameters (e.g., exceeds a predetermined length of the time of the on/off conditions, which may be longer than what the device is permitted to perform properly), the LOMM may cause an alert because the on/off conditions being outside the predetermined parameters may negatively affect the received ECG signals and/or negatively affect a potential therapy shock.

In another example, the LOMM may be configured to determine if an electrode is making poor contact with the skin. If a monitor electrode such as, but not limited to, an ECG electrode is making poor contact with the skin, the LOMM may be configured to determine that an impedance detected at the electrode may be unstable. As the person moves, the movement may cause the impedance detected at the electrode to "chatter" (i.e., bouncing back and forth between an "on" and an "off" conditions over a period of time similar to the previously described example). Even though this chatter may negatively affect the ECG signal received by the electrode, the LOMM may not cause an alert because if it is determined by the LOMM that the off condition does not persist continuously for more than 1 minute (e.g., a predetermined parameter), the LOMM may determine that an alert is not warranted. Accordingly, the LOMM may help avoid scenarios in which intermittent leads-off conditions may cause an alert, when the number of attachment integrity received are still within the predetermined parameters (i.e., even though a potential prevention of detecting an arrhythmia by the WCD may be detected, the proper functionality of the WCD may not be impaired).

In another example, if the electrode is on and off for 10 second periods (e.g., 50% duty cycle), which may prevent the medical device from detecting an arrhythmia, the LOMM may not cause an alert because the LOMM may determine that the intermittent leads-off conditions (i.e., the attachment integrity) are within the predetermined parameter.

In some examples, the LOMM may be configured to determine a number of intermittent leads-off conditions over a period of time. The LOMM may determine that if the number of intermittent leads-off conditions occur a number of times per period of time (e.g., 10 leads-off conditions in 10 minutes), the LOMM may be configured to determine that the attachment integrity may be outside the predetermined parameters causing the LOMM to issue an alert. In this example, the predetermined parameter may be 1 to 20 leads-off condition occurrences per minute. However, as may be appreciated, the predetermined parameters may be a wide variety of parameters such as, but not limited to, tolerances set by the device manufacturer, parameters set by a healthcare professional, parameters as prescribed by the device itself, and so forth. In some other example, various combinations of the amount of time the electrode may be off, the percentage of time that the electrode may be off, and the number of events may be utilized to set a threshold for detecting various leads-off conditions (i.e., predetermined parameter). Accordingly, the claimed subject matter is not limited in these respects.

In some examples, the LOMM may determine impedance at the electrode, where the determined impedance at the electrode may provide an indication of electrode contact quality (i.e., attachment integrity). The LOMM may determine whether the attachment integrity of the electrode may be determined to be as "definitely on", "definitely off", and/or "poor contact" based, at least in part, on the determined impedance at the electrode. For example, "definitely on" may have an impedance threshold of approximately 50 kilo ohm or less, "definitely off" may have an impedance threshold of approximately 1 mega ohm or less, and "poor contact" may have an impedance threshold of between approximately 50 kilo ohm—approximately 1 mega ohm. The determined impedance at the electrode may be sampled and averaged over a period of time to remove artifact such as, but not limited to, noise to facilitate accuracy of the determination. In this example, if the LOMM determines that the electrode may be in a "definitely off" condition (e.g., based, at least in part, on the determined impedance), the LOMM may cause an alert, which may be relatively rapid (e.g., approximately 1 minute). If the LOMM determines that the electrode may be in a "poor contact" condition (e.g., based, at least in part, on the determined impedance), the LOMM may cause an alert, which may be relatively slow (e.g., approximately 15 minutes). However, if the LOMM determines that the electrode may be in a "definitely on" condition (e.g., based, at least in part, on the determined impedance), the LOMM may not cause an alert.

In some examples, the LOMM may determine electrical signal noise associated with poor attachment integrity of the electrode. The LOMM may determine that the received indication of the attachment integrity of the electrode may be associated with electrical signal noise. In this example, the LOMM may not cause an alert because of the determination that the received indication of the poor attachment integrity may be associated with noise (i.e., the attachment integrity may be within the predetermined parameter). The electrical signal noise may be received over a period of time, as described.

Some examples of electrical signal noise that may be associated with electrodes may be found in U.S. Pat. No. 10,918,879B2 entitled "WEARABLE CARDIOVERTER DEFIBRILLATOR (WCD) SYSTEM REACTING TO HIGH-AMPLITUDE ECG NOISE", U.S. Pat. No. 10,960,220B2 entitled "WEARABLE CARDIOVERTER DEFIBRILLATOR (WCD) SYSTEM EVALUATING ITS ECG SIGNALS FOR NOISE ACCORDING TO TALL PEAK COUNTS", and U.S. Patent Application Pub. No. US20190030351A1 entitled "WEARABLE CARDIOVERTER DEFIBRILLATOR (WCD) SYSTEM REACTING TO HIGH-FREQUENCY ECG NOISE", all of which are incorporated herein in their entireties for all purposes.

In some examples, similar to the previously described examples of periodic determinations. In this example, because electrical signal noise (i.e., electrical signal artifacts) may be similar to receiving indications of the attachment integrity, the electrical signal noise may be periodic (intermittent) or continuous. If the LOMM receives periodic indications of the attachment integrity similar to the on/off conditions above, the LOMM may determine if the received indications of the attachment integrity may be electrical noise events. If it is determined that the attachment integrity may be electrical noise events, the LOMM may determine whether the noise events are outside the predetermined parameter or within the predetermined parameter. For example, a single electrical noise event that may not persist for long enough time period to be a problem (i.e., tolerance of the device and/or as prescribed by the healthcare professional) may not cause an alert. Conversely, if the single electrical noise event becomes periodic (i.e., repeated), the LOMM may cause an alert. Similar to the above described periodic conditions, the LOMM may a percentage of time of electrical signal noise events, a number of electrical signal noise events within a period of time, and/or similar methods.

Continuing with the non-limiting scenario, the LOMM may facilitate reduction and/or prevention of false alarms and/or excessive number of alerts. As may be appreciated, numerous false alarms and/or alerts may become annoying and may cause the person to ignore the alarms and/or alerts. Ignoring alarms and/or alerts may cause issues with the proper operation of the medical device because the person may not be aware that an alarm and/or alert may be due to actual attachment integrity of the electrode being outside the predetermined parameter.

In some examples, when the LOMM receives a number of indications of an attachment integrity of the electrode, the LOMM may determine an alert management scheme to facilitate optimization of number of necessary alerts (i.e., received indications of the attachment integrity is outside the predetermined parameter). One example of a scheme may be if the LOMM determines that the received indications of the attachment integrity are outside the predetermined parameter for a number of times (e.g., 3 alerts), the LOMM may cause an alert. Another example of a scheme may be that the LOMM may suspend alerts for a period of time (e.g., 1 hour), and subsequently, cause an alert or a series of alerts. Continuing with the scenario of the person wearing the WCD, if the person ignores alert, the LOMM may progressively increase the alerts, which may cause the person to recognize an urgency. Conversely, if the person continues to ignore the alerts, which may not be false alarms (i.e., the received indications of the attachment integrity are outside the predetermined parameter), the LOMM may be configured to transmit a message to another device such as, but not limited to, a mobile phone, a device located at a healthcare provider, etc.

In some embodiments, the LOMM may be configured to communicate a leads off condition utilizing various communication mediums. In one example, the LOMM may be configured to communicate the leads off condition via a visual indicator and/or a display. The display may be included in a mobile device (e.g., smart phone), included in a monitor of the medical device, and/or included as a healthcare facility monitor (e.g., healthcare clinic). Utilizing a display may facilitate a wide variety of communication capabilities. Additionally, a visual display utilized to facilitate an alert may be less intrusive and more appealing to the person than audible alerts.

The display may be utilized to display various information regarding the electrode (e.g., attachment integrity of the electrode). For example, the information displayed may include a text message (e.g., "leads off condition of an electrode detected"). Alternatively, the display may be utilized to graphically display the leads off condition such as, but not limited to, a color code and/or a scale, where the color code and/or scale may facilitate visual representation of the attachment integrity of the electrode and/or an electrical signal quality.

Continuing with the non-limiting scenario, as the person wears the WCD, the electrode may have fully detached from the skin for a long period of time (e.g., one hour). The LOMM may detect this detachment (i.e., receive the attachment integrity of the electrode on the skin) and may determine that the received indication of the attachment integrity is outside the predetermined parameter (i.e., fully detached for one hour). Responsive to the detected detachment of the electrode, the LOMM may communicate an alert to a smart phone belonging to the person. The alert may be in graphical form representing the attachment integrity such as, but not limited to, a graphical representation of the particular electrode blinking red to indicate that the particular electrode has an issue.

Utilization of a smart LOMM facilitates learning by the LOMM to help reduce false alarms and/or alerts, which may be ignored due to its frequency and annoyance. The learning process may include the LOMM being configured to receive and gather trend data regarding the indications of the attachment integrity over various time periods. As previously described, the LOMM may utilize measurement of impedance to facilitate determination of the attachment integrity. For example, the electrode can be categorized as "definitely on", "definitely off", or "poor contact" based, at least in part, on impedance. In the example scenario, the person wearing the WCD may go about various activities during various time periods (e.g., day, week, month, year, etc.). The LOMM may be configured to correlate various activities of the person with received indications of the attachment integrity (i.e., learn the person's activity during the time periods). For example, the LOMM may correlate the person's sleep patterns, where the LOMM may determine that as the person sleeps, the person may start sleeping on their back, but during the sleep cycle, the person may roll over on to their stomach, their side, etc. The changes in the person's sleeping position may be receive by the LOMM as indications the attachment integrity of the electrode, and in some of the received indications, the attachment integrity may be determined to be outside the predetermined parameter to activate an alert to communicate a leads off condition. However, since the LOMM may have learned the leads off condition may correspond to various movements during the person's sleep cycle, the LOMM may not cause an alert. The LOMM having learned a trend in the received number of attachment integrity (i.e., movements during sleep), may be smart enough to prevent awaking the person during their sleep. This example of the LOMM learning trends may be applicable to various activities of the person (e.g., running, walking, swimming, sitting, etc.) thereby helping to reduce false alarms and/or alerts (i.e., unnecessary alarms/alerts).

In another non-limiting example scenario utilizing the described various example embodiments, a medical device may be utilized to monitor an infant. The medical device may be a heart monitoring device such as, but not limited to, an ECG monitoring device. Accordingly, the ECG monitoring device may have at least a couple of electrodes to be attached to the skin of the infant. The ECG monitoring device may have its predetermined parameters set by a healthcare professional (e.g., pediatrician). As above, if it is determined that the received indications of the attachment integrity is outside the predetermined parameter, the LOMM may activate an alert on the monitor, the alert configured to communicate a leads off condition of the electrode from the skin to the infant (e.g., an alert sound).

Continuing with the non-limiting example scenario of the infant, the infant may be too young to appreciate the electrodes being on the skin, and accordingly, the infant may move irrespective of how their movements may affect the attachment of the electrode on the skin. For example, one can imagine that during the day, the infant may move around while sleeping. Without the smart LOMM described herein, the likelihood of the alert sound going off at least once or more times per day may be relatively high, which can cause some anxiety for the parent. However, utilizing the smart LOMM as described herein, the likelihood of the alert sound going off may be reduced facilitating a more accurate alert. As a result, the parent may not be inclined to ignore the alert or become stressed.

In yet another non-limiting scenario, one or more electrodes may be communicatively coupled to a medical device configured to measure electrical activities of the brain of a person. Here again, the smart LOMM described herein may facilitate a more accurate alert for a leads off condition of the one or more electrode from the skin and may help facilitate reduction of false alarms.

Turning now to FIG. 1, FIG. 1 illustrates a block diagram of a system for intelligent alerts for leads off conditions for an electrode of a medical device, in accordance with various embodiments. In FIG. 1, a system 100 may include a processor 102, one or more electrodes (hereon, electrode 104), and a storage medium 106, both communicatively coupled to the processor 102. Additionally, the processor 102 may include a leads off monitor module (hereon, LOMM 108). The electrode 104 may be configured to attach to a skin of a person. The LOMM 108 may be configured to facilitate the processor 102 to determine the various leads off conditions as described herein. In various embodiments, the system 100 may be included in a wide variety of medical devices that may utilize one or more electrodes configured to be attached to the skin such as, but not limited to, compact personal-use ECG devices, clinical ECG monitors, hospital-grade ECG monitors, brain activity monitors utilizing one or more electrodes for receiving electrical signals, respiration monitoring devices utilizing electrodes and/or sensor pads to detect respiration (e.g., determining impedance, utilizing ECG and/or pulse oximetry, and any combination), pulse oximetry devices (e.g., determining potential issues with the sensor on the skin), wearable devices (e.g., smart watches/band), wearable medical devices (WMDs), wearable cardioverter defibrillator (WCDs), and so forth. Some further details of the system 100 may be found with respect FIG. 7.

In FIG. 1, the storage medium 106 may include information such as, but not limited to, predetermined parameters, activity information, trend data, periodic information, etc. The processor 102 may be a wide variety of machine learning capable processors to facilitate at least some of the functionality described herein such as, but not limited to, machine learning capable processors available from Intel Corporation of Santa Clara, California (e.g., Nervana™ type processors), available from Nvidia Corporation of Santa Clara, California (e.g., Volta™ type processors), available from Apple Company of Cupertino, California (e.g., A11 Bionic™ type processors), available from Huawei Technologies Company of Shenzen, Guangdong, China (e.g., Kirin™ type processors), available from Advanced Micro Devices, Inc. of Sunnyvale, California (e.g., Radeon Instinct™ type processors), available from Samsung of Seoul, South Korea (e.g., Exynos™ type processors), and so forth. Accordingly, the claimed subject matter is not limited in these respects.

Figure 2:
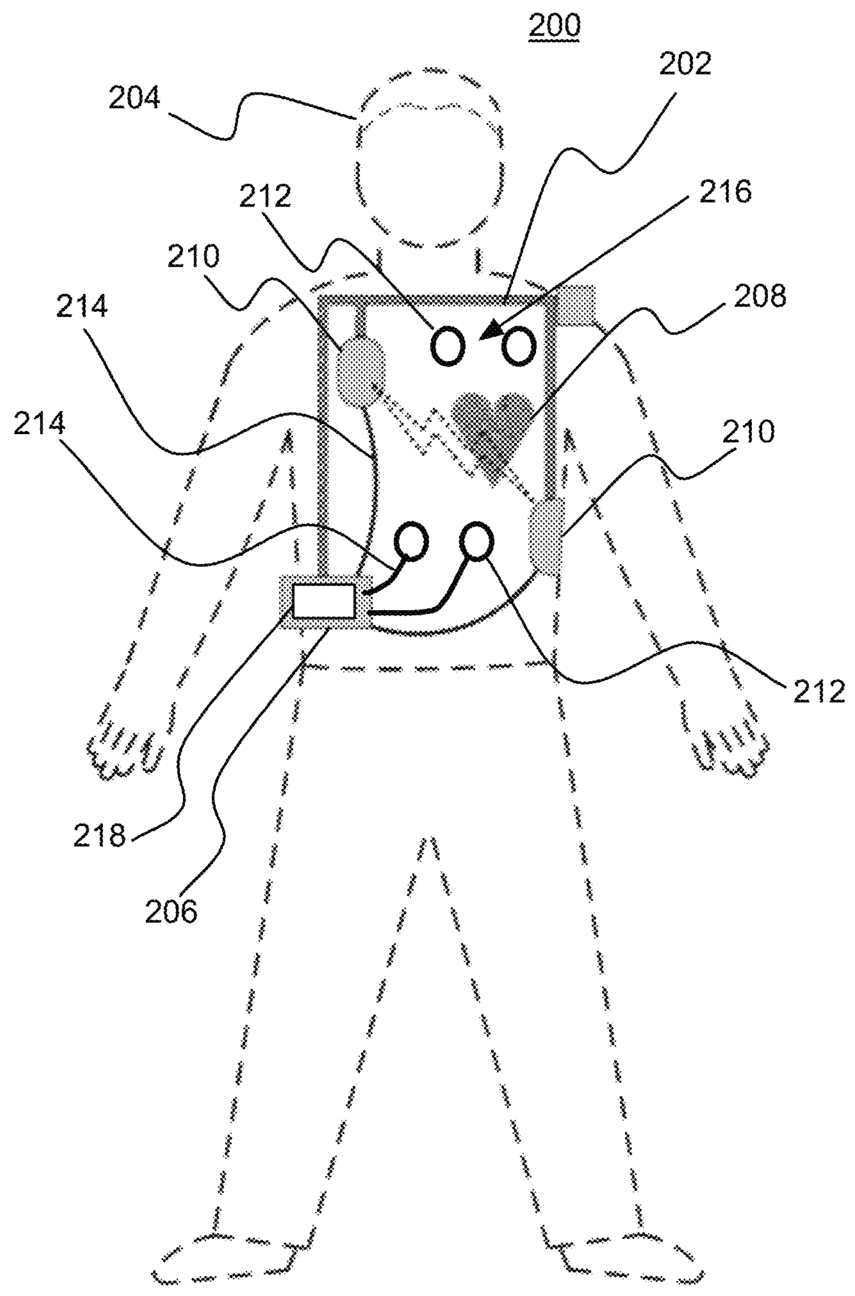
FIG. 2 illustrates an example of a medical device that may utilize one or more electrodes, in accordance with at least one or more example embodiments.

FIG. 2 illustrates an example of a medical device that may utilize one or more electrodes, in accordance with at least one or more example embodiments. In FIG. 2, a medical device may be a wearable medical device (WMD), which may be configured to facilitate monitoring and treatment of a person's heart such as, but not limited to, a wearable cardioverter defibrillator (WCD) 200. The WCD 200 may be included in a support structure 202, which may be configured to be worn by a person 204. The WCD 200 may include various electronic components to facilitate the functionality of the WCD 200 as a heart monitoring and defibrillator device. The various electronic components may be illustrated as a WCD module (hereon a WCD monitor 206). The WCD 200 may include two therapy electrodes configured to defibrillate a person's heart 208, defibrillator electrodes 210, and a number of monitoring electrodes 212 configured to detect and measure the person's electrical heart activity (e.g., electrocardiogram or ECG). As shown, the monitoring electrodes 212 and the defibrillator electrodes 210 may be located proximate to the person's heart 208 and chest area 216. The monitoring electrodes 212 and the defibrillator electrodes 210 may be communicatively coupled to the WCD monitor 206 via a number of electrical leads 214. Additionally, shown in FIG. 2, the WCD monitor 206 may include a leads off monitor module (LOMM 218).

In FIG. 2, the support structure 202 may be in the form of a garment configured to be worn by the person 204. In some examples, the monitoring electrodes 212 and the defibrillator electrodes 210, shown in FIG. 2, may be configured to be wirelessly coupled with the WCD monitor 206.

As described herein, the LOMM 218 included in the WCD monitor 2 may be configured to receive a number of indications of attachment integrity of at least one of the electrodes 210 and 212. Responsive to a determination that the received number of indications are outside the predetermined parameter, the LOMM 208 may be configured to activate an alert. The alert may be configured to communicate a leads off condition of at least one of the electrodes 210 and 212 from the skin of the person 204.

In FIG. 2, when the person 204 moves while wearing the WCD 200, one or more of the electrodes 210 and 212 may start to lift off of the skin, which may cause the LOMM 218 to receive the indications of the attachment integrity. However, as described herein, the LOMM 218 determine if the attachment integrity of the one or more electrodes 210 and 212 (having started to lift off the skin) is within the predetermined parameter (e.g., for various time periods within the tolerance of the device). If it is determined that the attachment integrity is within the predetermined parameter, the LOMM 218 may not cause an alert. Conversely, if it is determined that the attachment integrity is outside the predetermined parameter, the LOMM 218 may cause an alert.

In some examples, the alert may be a visual alert such as, but not limited to, a light indicator. In some examples, the alert may be a visual alert on a display. In some further examples, the alert may be an audio alert such as, but not limited to, an alarm. In some embodiments, the one more example alerts may be included in the WCD monitor 206. In some embodiments, the one or more example alerts may be included in the support structure 202. In some further embodiments, the one or more example alerts may be included in a separate device such as, but not limited to, a smart phone, a wireless display device, a computing device, etc. In these examples, the LOMM 218 may cause the alert to be transmitted to the separate device via a wireless protocol such as, but not limited to, Wi-Fi, Bluetooth, Near-Field Communication, Radio-frequency identification (RFID), various IEEE 802 based wireless communication including Zigbee, cellular wireless communication, etc. Accordingly, the claimed subject matter is not limited in these respects.

It should be appreciated after review of this disclosure that it is contemplated within the scope and spirit of the present disclosure that the claimed subject matter may include a wide variety of healthcare devices. As described above, the WCD 200 is only but one example of a medical device utilizing electrodes 210 and 212. The description herein may equally apply to a wide variety of medical devices utilizing one or more electrodes 210 and 212 such as, but not limited to, ECG monitoring medical devices, brain activity monitoring devices, respiration monitoring devices, etc. Accordingly, the claimed subject matter is not limited in these respects.

Figure 3:
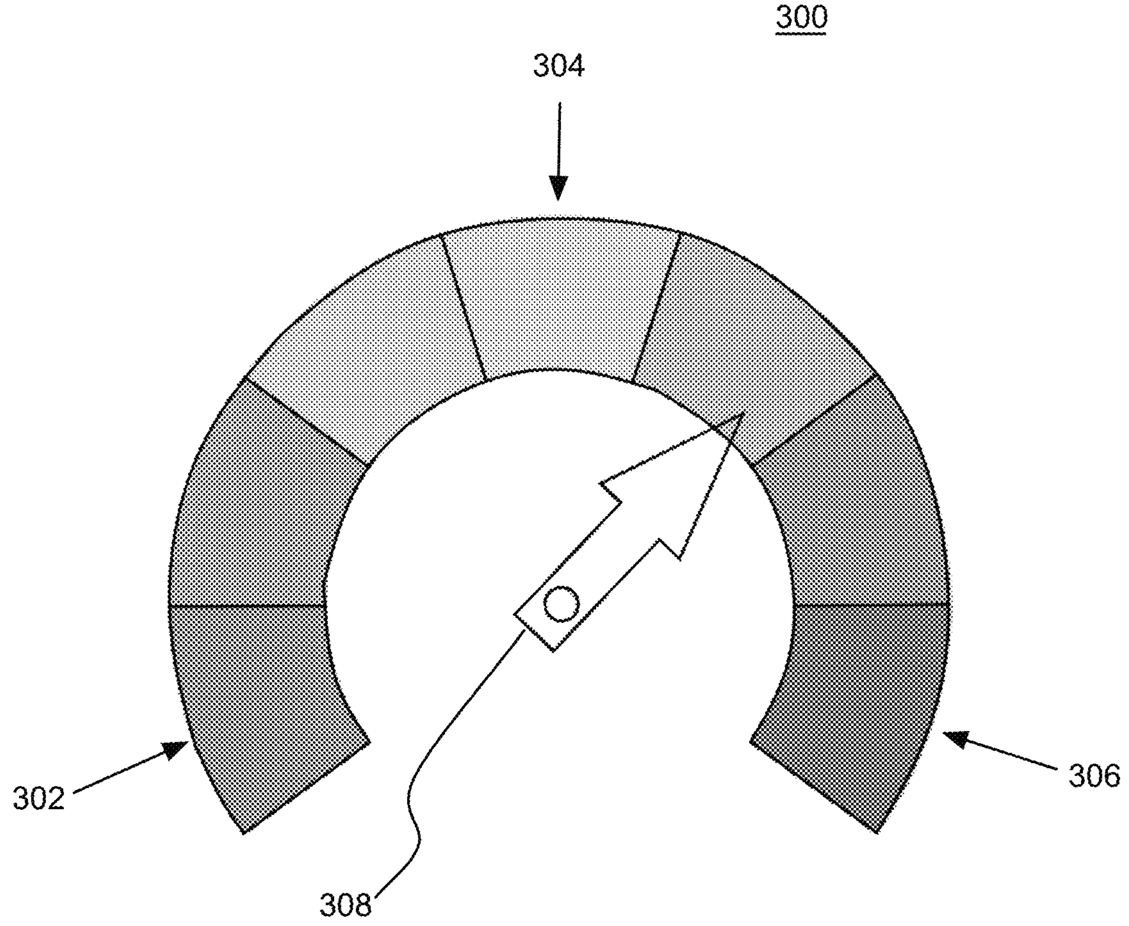
FIG. 3 illustrates a visual indication of attachment integrity, in accordance with some embodiments.

FIG. 3 illustrates a visual indication of attachment integrity, in accordance with some embodiments. In FIG. 3, a visual indicator may be configured to display attachment integrity as a circular dial (e.g., gauge 300 having color gradients (e.g., scale), green 302 to yellow 304 to red 306, and in between these colors, gradients may be indicated. The gauge 300 may include a graphical representation of a dial needle 308 located at the center of the gauge 300. In FIG. 3, the green color 302 on the gauge 300 may indicate a good contact of one or more electrodes on the skin, while the red color 302 on the gauge 300 may indicate a poor contact of one or more electrodes on the skin. The yellow color 304 may indicate a marginal contact of one or more electrodes on the skin. Additionally, the gauge 300 may be configured to indicate electrical signal quality and/or attachment integrity. Accordingly, the green color 302 may indicate good electrode contact, red may indicate poor contact may require corrective action, which may cause an alert, and yellow may indicate a chronic condition that may not ideal but may be tolerated, in accordance with various embodiments. Indications may be facilitated by the dial needle 308 being configured to rotate around the gauge 300 to provide a visual indication of attachment integrity in gradient form.

The gauge 300 may be displayed on a variety of display devices such as a display included in a medical device monitor (e.g., WCD monitor), on a smart phone display, on tablet display, and so forth and may be communicated via wired and/or wirelessly. Additionally, the gauge 300 may be configured to display the attachment integrity utilizing a wide variety of shapes such as, substantially rectangular, substantially pyramidal, etc. Accordingly, the claimed subject matter is not limited in this respect. Further, the visual display of the gauge 300 may be included a visual display of the actual electrode associated with the gauge. For example, a visual display may include more than one gauge 300, which may include an indication of an association of the gauge with a particular electrode. In another example, the gauge 300 may include on the gauge an indication of which one or more electrodes and their attachment integrity and/or electrical signal quality.

Figure 4:
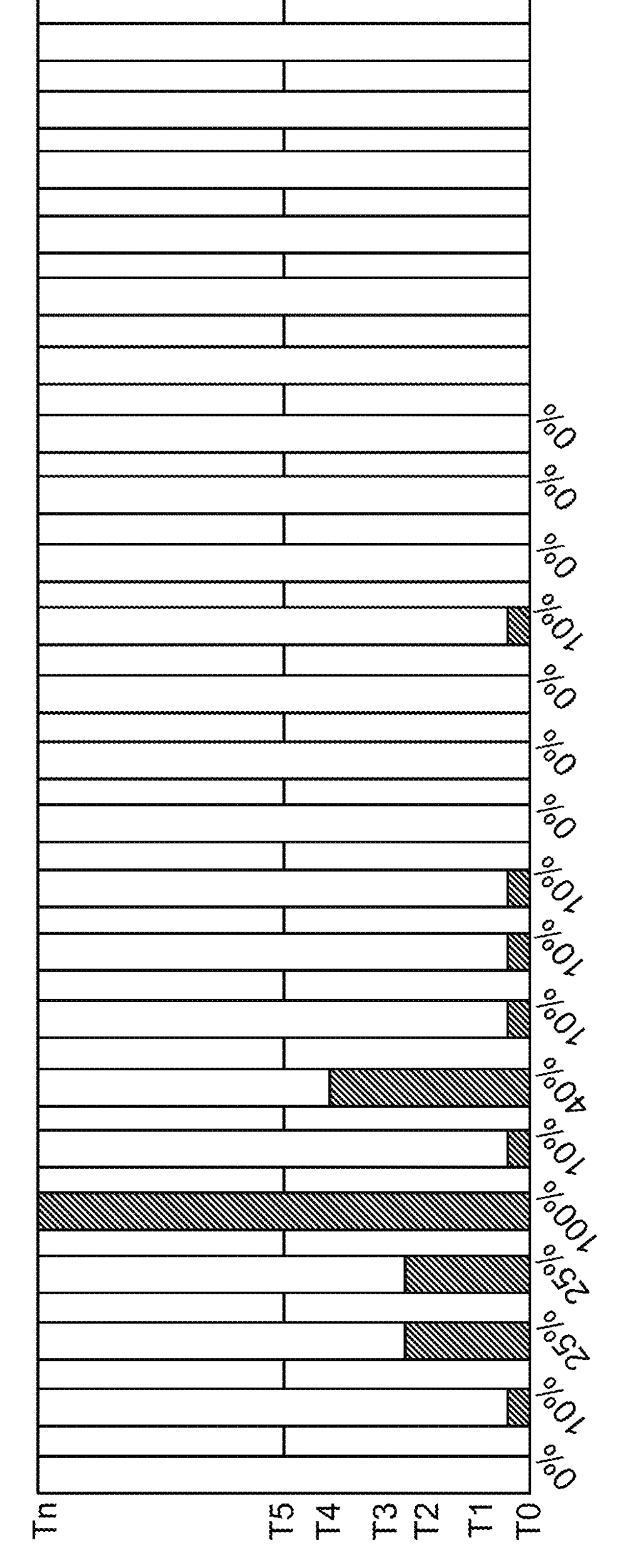
FIG. 4 illustrates a graphical representation of trend of leads off conditions, in accordance with various embodiments.

FIG. 4 illustrates a graphical representation of trend of leads off conditions, in accordance with various embodiments. In FIG. 4, a trend data may be displayed a as a trend graph (e.g., histogram 400). Utilizing various measurements, the LOMM 108 may be configured to determine categorize one or more electrodes as "definitely on", "definitely off", or "poor contact" based, at least in part, on some form of electrical contact quality (e.g., impedance). Accordingly, the histogram 400 may be a visual representation of the presence of leads-off or noise alerts. In FIG. 4, the histogram 400 may show an example of electrode leads-off alert monitoring over a time T0 to Tn in a day, where Tn may be a number of minutes (e.g., 10 minutes) or any predetermined time period. In FIG. 4, Tn may represent a 24-hour day, and accordingly, when the LOMM 108 causes a leads-off alert, the information may be captured and displayed as the histogram 400. Additionally, the histogram 400 may provide a visualization of trend data over a wear time (e.g., WMD) during the time between T0 and Tn, where Tn may be a 24-hour day and/or over many days as a person may wear the medical device. In one example, a person may be new to a wearable monitoring device such as, but not limited to, a WCD, and the histogram 400 may be facilitate representation of proper wearing of the medical device. For example, improper wearing and/or fit of the medical device may be resolved with simple adjustments, guidance, instructions, etc. In such cases, causes may be determined and future preventative or ameliorative actions taken.

Further, the leads off alert information may be further correlated with other events and/or activities that may be occurring substantially at the same time. For example, activities such as, but not limited to, steps taken in a particular day and/or wear time may be correlated. If no steps were taken and the leads show as off for 24 hours, the person may not be wearing the device properly. Additionally, this information may be verified by physiological data such as, but not limited to, an ECG recorded during that time.

As a result, a smart LOMM may help facilitate determination of potential causes of electrode leads off conditions and to facilitate smart leads off information monitoring and alerting.

Figure 5:
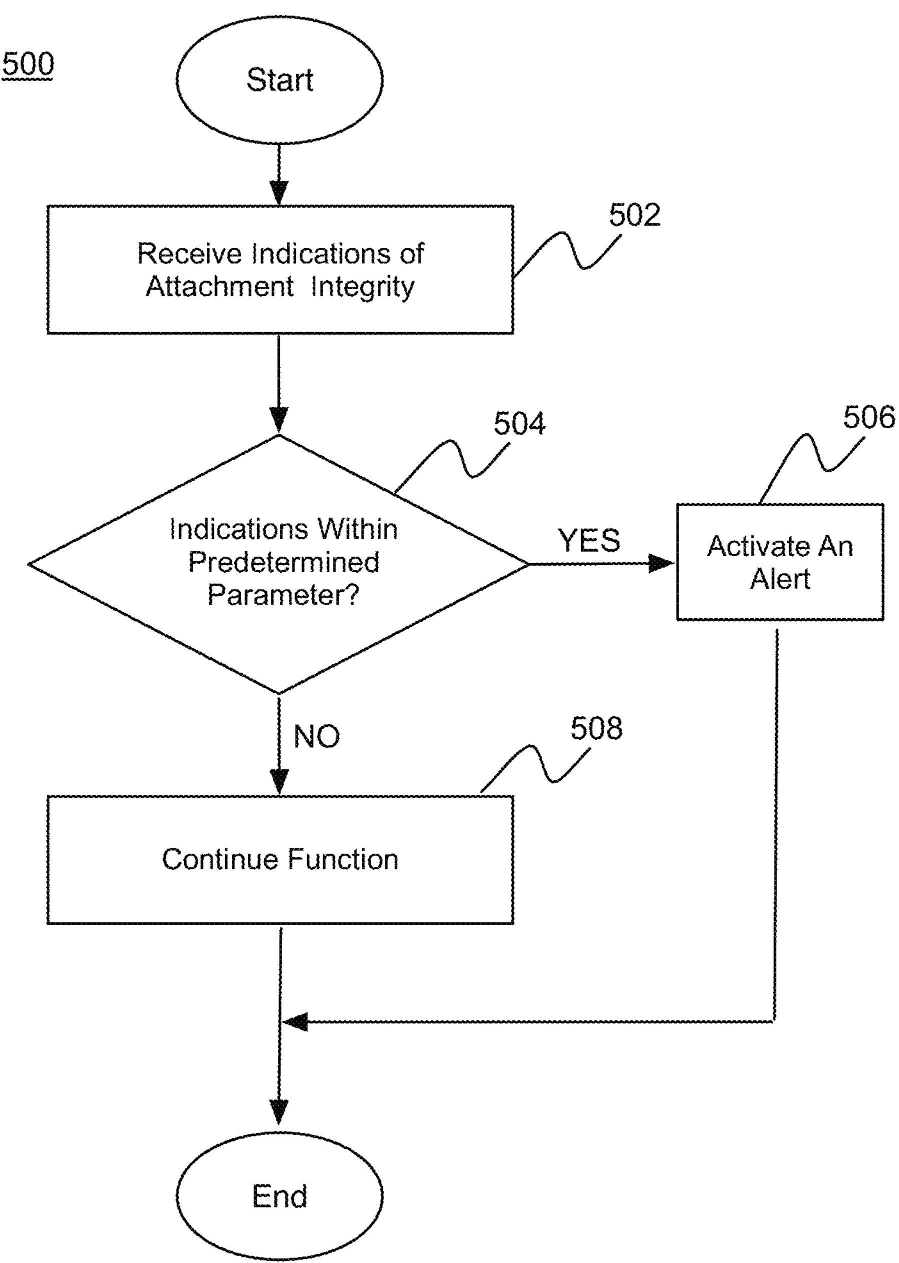
FIG. 5 illustrates an operational flow for a smart leads off monitoring module, arranged in accordance with at least some embodiments described herein.

FIG. 5 illustrates an operational flow for a smart leads off monitoring module, arranged in accordance with at least some embodiments described herein. In some portions of the description, illustrative implementations of the method are described with reference to the elements depicted in FIGS. 1 and 2. However, the described embodiments are not limited to these depictions.

Additionally, FIG. 5 employs block diagrams to illustrate the example methods detailed therein. These block diagrams may set out various functional block or actions that may be described as processing steps, functional operations, events and/or acts, etc., and may be performed by hardware, software, and/or firmware. Numerous alternatives to the functional blocks detailed may be practiced in various implementations. For example, intervening actions not shown in the figures and/or additional actions not shown in the figures may be employed and/or some of the actions shown in one figure may be operated using techniques discussed with respect to another figure. Additionally, in some examples, the actions shown in these figures may be operated using parallel processing techniques. The above described, and other not described, rearrangements, substitutions, changes, modifications, etc., may be made without departing from the scope of the claimed subject matter.

In some examples, operational flow 500 may be employed as part of medical device having electrical signal monitoring capabilities. Beginning at block 502 ("Receive Indications of Attachment Integrity"), a healthcare medical device such as, but not limited to, a healthcare medical device configured to monitor and/or provide therapy electrical signals via one or more electrodes may receive an indication that the condition of the attachment of the one or more electrode may have changed (e.g., started lifting off the skin or electrical signal may have issues such as noise or signal strength). The received indications may be received by a leads off monitoring module (LOMM).

Continuing from block 502 to decision diamond 504 ("Indications Within Predetermined Parameter?"), the LOMM may determine if the received indications of the attachment integrity are within a predetermined parameter. The predetermined parameter may be a variety of parameters as disclosed herein (e.g., periodic attachment issues, partially lifted off the skin but still within design parameters of the medical device and/or prescribed by a medical professional, medical device tolerances, etc.).

If the LOMM determines that the received indication of the attachment integrity is outside the predetermined parameter ("YES"), the LOMM may cause an alert, from decision diamond 504 to block 506 ("Activate an Alert"). Conversely, if the LOMM determines that the received indication of the attachment integrity is not outside the predetermined parameter ("NO"), the LOMM may not cause an alert, and accordingly, the medical device may continue to function as normal, from decision diamond 504 to block 508 ("Continue Function").

In general, the operational flow described with respect to FIG. 5 and elsewhere herein may be implemented as a computer program product, executable on any suitable computing system, or the like. For example, a computer program product for determining leads off monitoring device may be provided. Example computer program products may be described with respect to FIG. 6 and elsewhere herein.

FIG. 6 illustrates an example computer program product 600, arranged in accordance with at least some embodiments described herein. Computer program product 600 may include machine readable non-transitory medium having stored therein instructions that, when executed, cause the machine to learn whether to activate an alarm, according to the processes and methods discussed herein. Computer program product 600 may include a signal bearing medium 602. Signal bearing medium 602 may include one or more machine-readable instructions 604 which, when executed by one or more processors, may operatively enable a computing device to provide the functionality described herein. In various examples, the devices discussed herein may use some or all of the machine-readable instructions.

In some examples, the machine readable instructions 604 may include a leads off monitoring module (LOMM) configured to receive a plurality of indications of attachment integrity of an electrode on a skin of a person, the plurality of indications. In some examples, the machine readable medium 604 may facilitate the LOMM to determine if the received plurality of indications of attachment are within a predetermined parameter. In some examples, the machine readable medium 604 may, responsive to a determination that the received plurality of indications of attachment integrity are outside the predetermined parameter, facilitate the LOMM to activate an alert, the alert configured to communicate a leads off condition of the electrode from the skin of the person.

In some implementations, signal bearing medium 602 may encompass a computer-readable medium 606, such as, but not limited to, a hard disk drive, a Compact Disc (CD), a Digital Versatile Disk (DVD), a Universal Serial Bus (USB) drive, a digital tape, memory, etc. In some implementations, the signal bearing medium 602 may encompass a recordable medium 608, such as, but not limited to, memory, read/write (R/W) CDs, R/W DVDs, etc. In some implementations, the signal bearing medium 602 may encompass a communications medium 610, such as, but not limited to, a digital and/or an analog communication medium (e.g., a fiber optic cable, a waveguide, a wired communication link, a wireless communication link, etc.). In some examples, the signal bearing medium 602 may encompass a machine readable non-transitory medium.

In general, the methods described with respect to FIG. 5 and elsewhere herein may be implemented in any suitable computing system. Example systems may be described with respect to FIG. 7 and elsewhere herein. In general, the system may be configured to facilitate a smart leads off monitoring module.

Figure 7:
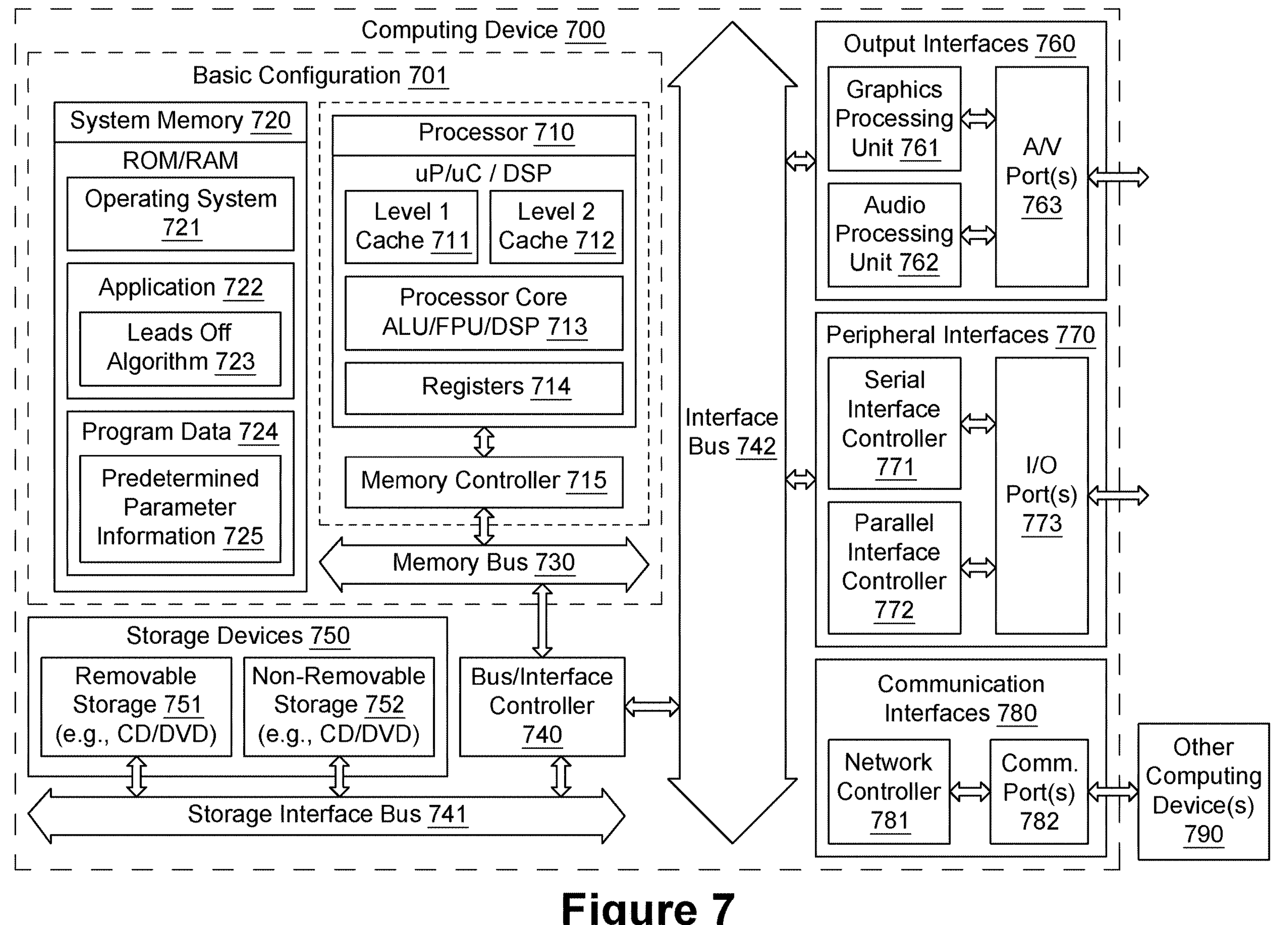
FIG. 7 is a block diagram illustrating an example computing device, such as might be embodied by a person skilled in the art, which is arranged in accordance with at least some embodiments of the present disclosure.

FIG. 7 is a block diagram illustrating an example computing device 700, such as might be embodied by a person skilled in the art, which is arranged in accordance with at least some embodiments of the present disclosure. In one example configuration, computing device 700 may include one or more processors 710 and system memory 720. A memory bus 730 may be used for communicating between the processor 710 and the system memory 720.

Depending on the desired configuration, processor 710 may be of any type including but not limited to a microprocessor (μP), a microcontroller (μC), a digital signal processor (DSP), or any combination thereof. Processor 710 may include one or more levels of caching, such as a level one cache 711 and a level two cache 712, a processor core 713, and registers 714. The processor core 713 may include an arithmetic logic unit (ALU), a floating point unit (FPU), a digital signal processing core (DSP Core), or any combination thereof. A memory controller 715 may also be used with the processor 710, or in some implementations the memory controller 715 may be an internal part of the processor 710.

Depending on the desired configuration, the system memory 720 may be of any type including but not limited to volatile memory (such as RAM), non-volatile memory (such as ROM, flash memory, etc.) or any combination thereof. System memory 720 may include an operating system 721, one or more applications 722, and program data 724. Application 722 may include leads off algorithm 723 that is arranged to perform the functions as described herein including the functional blocks and/or actions described. Program Data 724 may include, among other information described, predetermined parameter data 725 for use with leads off algorithm 723. In some example embodiments, application 722 may be arranged to operate with program data 724 on an operating system 721 such that implementations of leads off monitoring module having determination capabilities may be provided as described herein. For example, apparatus described in the present disclosure may comprise all or a portion of computing device 700 and be capable of performing all or a portion of application 722 such that determining leads off conditions as described herein. This described basic configuration is illustrated in FIG. 7 by those components within dashed line 701.

Computing device 700 may have additional features or functionality, and additional interfaces to facilitate communications between the basic configuration 701 and any required devices and interfaces. For example, a bus/interface controller 740 may be used to facilitate communications between the basic configuration 701 and one or more data storage devices 750 via a storage interface bus 741. The data storage devices 750 may be removable storage devices 751, non-removable storage devices 752, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 720, removable storage 751 and non-removable storage 752 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 700. Any such computer storage media may be part of device 700.

Computing device 700 may also include an interface bus 742 for facilitating communication from various interface devices (e.g., output interfaces, peripheral interfaces, and communication interfaces) to the basic configuration 701 via the bus/interface controller 740. Example output interfaces 760 may include a graphics processing unit 761 and an audio processing unit 762, which may be configured to communicate to various external devices such as a display or speakers via one or more A/V ports 763. Example peripheral interfaces 760 may include a serial interface controller 771 or a parallel interface controller 772, which may be configured to communicate with external devices such as input devices (e.g., keyboard, mouse, pen, voice input device, touch input device, etc.) or other peripheral devices (e.g., printer, scanner, etc.) via one or more I/O ports 773. An example communication interface 780 includes a network controller 781, which may be arranged to facilitate communications with one or more other computing devices 790 over a network communication via one or more communication ports 782. A communication connection is one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), infrared (IR) and other wireless media. The term computer readable media as used herein may include both storage media and communication media.

Computing device 700 may be implemented as a portion of a small-form factor portable (or mobile) electronic device such as a cell phone, a personal data assistant (PDA), a personal media player device, a wireless web-watch device, a personal headset device, an application specific device, or a hybrid device that includes any of the above functions. Computing device 700 may also be implemented as a personal computer including both laptop computer and non-laptop computer configurations. In addition, computing device 700 may be implemented as part of a wireless base station or other wireless system or device.

Figure 8:
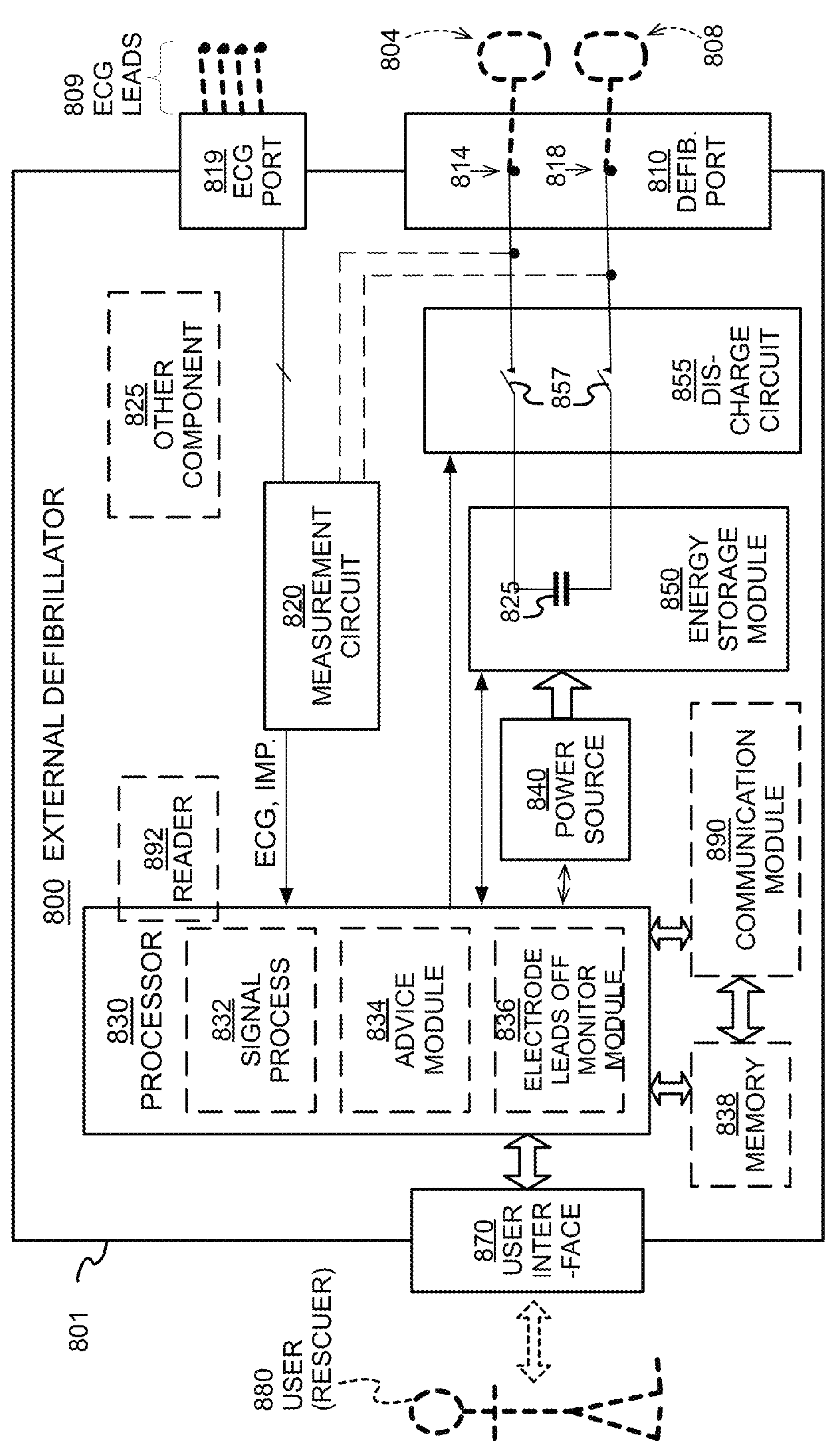
FIG. 8 is a block diagram illustrating components of a heart monitoring device, which may be used with various embodiments.

FIG. 8 is a block diagram illustrating components of a heart monitoring device 800, which may be used with various embodiments. These components may be, for example, a medical device 100 (shown in FIG. 1) and wearable medical device 200 (shown in FIG. 2). For simplicity, the medical device may be an example of defibrillator device.

The defibrillator device 800 may be intended for use by a user 880 (e.g., the person 204 shown in FIG. 2). The defibrillator device 800 may typically include a defibrillation port 810, such as a socket in housing 801. The defibrillation port 810 may include nodes 814 and 818. One or more electrodes 804 and 808, which may be similar to electrodes 104 (shown in FIG. 1) and electrodes 210 and 212 (shown in FIG. 2) may be plugged in to the defibrillation port 810, so as to make electrical contact with nodes 814 and 818, respectively. It may also be possible that the electrodes 804 and 808 may be connected continuously to the defibrillation port 810, etc. Either way, the defibrillation port 810 may be used for guiding via the electrodes 804 and 808 to the person 880 an electrical charge that may have been stored in the defibrillator device 800, as described herein.

If the defibrillator device 800 comprise of a heart monitoring component, as was described herein, the defibrillator device 800 may also have an ECG port 819 in the housing 801, for receiving ECG leads 809. The ECG leads 809 may facilitate sensing of an ECG signal (e.g., a 12-lead signal or from a different number of lead signals), and electrode attachment integrity may be determined from the ECG signal, in accordance with the various embodiments disclosed herein. Moreover, a heart monitoring component could have additional ports (not shown), and the other component 825 may be configured to utilize the electrical signal (e.g., ECG signal, impedance, etc. to facilitate determination of electrode leads off from the skin of the user 880), in accordance with various embodiments.

The defibrillator 800 also may include a measurement circuit 820. The measurement circuit 820 may receive physiological signals from the ECG port 819, and also from other ports, if provided (e.g., previously described lead-off circuitry). The circuit 820 may render detected physiological signals and their corresponding information. The information may be in the form of data, or other signals, etc.

The measurement circuit 820 may obtain physiological signals through the nodes 814 and 818 instead, when the electrodes 804 and 808 are attached to the person 880 (i.e., the skin), as previously described. In these cases, a person's ECG signal may be detected as a voltage difference between the electrodes 804 and 808. Additionally, the impedance between the electrodes 804 and 808 may detect, among other things, whether the electrodes 804 and 808 have been inadvertently disconnected from the skin of the person 880 (e.g., partially lifted off, fully lifted off, periodically lifted off, etc. as previously described), in accordance with various embodiments.

The defibrillator 800 may also include a processor 830. The processor 830 may be implemented in a wide variety of manners for causing actions and operations to be performed. Some examples may include digital and/or analog processors such as microprocessors and digital-signal processors (DSPs), controllers such as microcontrollers, software running in a machine environment, programmable circuits such as Field Programmable Gate Arrays (FPGAs), Field-Programmable Analog Arrays (FPAAs), Programmable Logic Devices (PLDs), Application Specific Integrated Circuits (ASICs), and so on or any combination thereof.

The processor 830 may include a number of modules. One example module may be a signal processing module 832, which may detect outputs from the measurement circuit 820. The signal processing module 832 may include electronic components configured to determine electrode leads off conditions such as, but not limited to the various processes described above. Accordingly, indications of one or more electrode attachment integrity may be utilized to determine whether the attachment integrity is within predetermined parameters, where if an alert is caused by a LOMM, the alert may be configured to communicate to the person 880 and/or other personnel (e.g., medical professional, emergency personnel, guardian, medical device manufacturer, etc.) that an electrode leads off condition is present.

In another example, advice module 834 may provide advice based, at least in part, on outputs of signal processing module 832. The advice module 834 may include an algorithm such as, but not limited to, Shock Advisory Algorithm, implement decision rules, and so on. For example, the advice may be to shock, to not shock, to administer other forms of therapy, provide an indication to confirm a health status of the person 880 (e.g., determine whether the person 880 is experiencing perfusing or non-perfusing ventricular tachycardia (VT), and so on. If the advice is to shock, some defibrillator examples may report the advice to the user and prompt them to do it. In other examples, the defibrillator device may execute the advice by administering the shock. If the advice is to administer CPR, the defibrillator 800 may further issue prompts for administrating CPR, and so forth. Examples of Shock Advisory Algorithm may be found in U.S. patent application Ser. No. 15/421,165, filed Jan. 31, 2017 (now issued as U.S. Pat. No. 10,016,614) titled Wearable cardioverter defibrillator (WCD) system making shock/no shock determinations by aggregating aspects of multiple patient parameters, which is incorporated by reference in its entirety for all purposes.

The processor 830 may include additional modules, such as module 836 for various other functions such as, but not limited to, an electrode leads off monitor module (LOMM) 836, as described herein.

In an example, the defibrillator device 800 may include a memory 838, which may work together with the processor 830. The memory 838 may be implemented in a wide variety of manners. For example, the memory 838 may be implemented such as, but not limited to, nonvolatile memories (NVM), read-only memories (ROM), random access memories (RAM), and so forth or any combination thereof. The memory 838 may include programs for the processor 830, and so on. For example, the memory 838 may include ECG signals for determining a respiration rate post-event. The programs may include operational programs executed by the processor 830 and may also include protocols and methodologies so that decisions may be made by advice module 834. Additionally, the memory 838 may store various prompts for the user 880, etc. Moreover, the memory 838 may store a wide variety of information (i.e., predetermined parameter data) such as, but not limited to information regarding the person 880.

The defibrillator 800 may also include a power source 840. In order to facilitate portability of defibrillator device 800, the power source 840 may include a battery type device. A battery type device may be implemented as a battery pack, which may be rechargeable or not-rechargeable. At times, a combination of rechargeable and non-rechargeable battery packs may be utilized. Examples of power source 840 may include AC power override, where AC power may be available, and so on. In some examples, the processor 830 may control the power source 840.

Additionally, the defibrillator device 800 may include an energy storage module 850. The energy storage module 850 may be configured to store some electrical energy (e.g., when preparing for sudden discharge to administer a shock). The energy storage module 850 may be charged from the power source 840 to an appropriate level of energy, as may be controlled by the processor 830. In some implementations, the energy storage module 850 may include one or more capacitors 852, and the like.

The defibrillator 800 may include a discharge circuit 855. The discharge circuit 855 may be controlled to facilitate discharging of the energy stored in energy storage module 850 to the nodes 814 and 818, and also to electrodes 104 (shown in FIG. 1) and electrodes 210 and 212 (shown in FIG. 2). The discharge circuit 855 may include one or more switches 857. The one or more switches 857 may be configured in a number of manners such as, but not limited to, an H-bridge, and so forth.

The defibrillator device 800 may further include a user interface 870 for the user 880. The user interface 870 may be implemented in a variety of manners. For example, the user interface 870 may include a display screen capable of displaying what is detected and measured, provide visual feedback to the user 880 for their resuscitation attempts, and so forth. The user interface 870 may also include an audio output such as, but not limited to, a speaker to issue audio prompts, etc. The user interface 870 may additionally include various control devices such as, but not limited to, pushbuttons, keyboards, switches, track pads, and so forth. Additionally, the discharge circuit 855 may be controlled by the processor 830 or directly by the user 880 via the user interface 870, and so forth.

Additionally, the defibrillator device 800 may include other components. For example, a communication module 890 may be provided for transmitting ECG signals stored on the defibrillator device 800 to be downloaded and processed as described above. Such communication may be performed wirelessly, or via wire, or by infrared communication, near field communication (NFC), Bluetooth, WiFi, and so forth. Accordingly, information may be communicated, such as person data, incident information, therapy attempted, CPR performance, ECG information, and so forth.

A feature of a defibrillator device may be CPR related prompting. CPR prompts may be issued to the user 880 visually or by audio facilitating assistance in the administration of CPR by the user 880. Examples may be found in U.S. Pat. Nos. 6,334,070 and 6,356,785.

It should be appreciated after review of this disclosure that it is contemplated within the scope and spirit of the present disclosure that the claimed subject matter may include a wide variety of healthcare devices. Accordingly, the claimed subject matter is not limited in these respects.

Some portions of the foregoing detailed description are presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm is here, and generally, considered to be a self-consistent sequence of operations or similar processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, as apparent from the following discussion, it is appreciated that throughout this specification discussion utilizing terms such as "processing," "computing," "calculating," "determining" or the like refer to actions or processes of a computing device that manipulates or transforms data represented as physical electronic or magnetic quantities within memories, registers, or other information storage devices, transmission devices, or display devices of the computing device.

Claimed subject matter is not limited in scope to the particular implementations described herein. For example, some implementations may be in hardware, such as those employed to operate on a device or combination of devices, for example, whereas other implementations may be in software and/or firmware. Likewise, although claimed subject matter is not limited in scope in this respect, some implementations may include one or more articles, such as a signal bearing medium, a storage medium and/or storage media. This storage media, such as CD-ROMs, computer disks, flash memory, or the like, for example, may have instructions stored thereon that, when executed by a computing device such as a computing system, computing platform, or other system, for example, may result in execution of a processor in accordance with claimed subject matter, such as one of the implementations previously described, for example. As one possibility, a computing device may include one or more processing units or processors, one or more input/output devices, such as a display, a keyboard and/or a mouse, and one or more memories, such as static random access memory, dynamic random access memory, flash memory, and/or a hard drive.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be affected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skilled in the art in light of this disclosure. In addition, those skilled in the art will appreciate that the mechanisms of the subject matter described herein are capable of being distributed as a product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a flexible disk, a hard disk drive (HDD), a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Reference in the specification to "an implementation," "one implementation," "some implementations," or "other implementations" may mean that a particular feature, structure, or characteristic described in connection with one or more implementations may be included in at least some implementations, but not necessarily in all implementations. The various appearances of "an implementation," "one implementation," or "some implementations" in the preceding description are not necessarily all referring to the same implementations.

While certain exemplary techniques have been described and shown herein using various methods and systems, it should be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter is not limited to the particular examples disclosed, but that such claimed subject matter also may include all implementations falling within the scope of the appended claims, and equivalents thereof.

What is claimed:

1. An electrical signal monitoring medical system, comprising:
- at least one electrode, the at least one electrode configured to be attachable to a skin of a person and configured to receive electrical signals; and
- a processor communicatively coupled to the at least one electrode, the processor configured to:
  - determine an impedance at the at least one electrode, wherein the determined impedance corresponds to an indication of attachment integrity of the at least one electrode on the skin;
  - categorize the at least one electrode into a category of a plurality of categories based, at least in part, on the determined impedance at the at least one electrode, each of the plurality of categories being associated with the attachment integrity, wherein the plurality of categories of the at least one electrode comprises:
    - a first category of the at least one electrode categorized based on a comparison of the determined impedance at the at least one electrode with a first impedance threshold,
    - a second category of the at least one electrode categorized based on a comparison of the determined impedance at the at least one electrode with a second impedance threshold, and
    - a third category of the at least one electrode categorized based on a comparison of the determined impedance at the at least one electrode with a third impedance threshold,
  - responsive to a determination that the category of the at least one electrode is the first category, activate a first alert of a plurality of alerts;
  - responsive to a determination that the category of the at least one electrode is the second category, activate a second alert of the plurality of alerts, wherein the second alert is activated slower than the first alert, and
  - wherein the processor is further configured to abstain from activating an alert responsive to a determination of the third category of the at least one electrode;
  - responsive to the activation of the first or the second alert, cause a corrective action to be performed to restore the attachment integrity of the at least one electrode on the skin; and
  - cause a therapy to be provided to the person to treat a cardiac condition of the person after the corrective action is performed.

2. The electrical signal monitoring medical system of claim 1, wherein the first impedance threshold corresponds to a value equal to or less than 1 mega ohm, the second impedance threshold corresponds to a range between 50 kilo ohm and 1 mega ohm, and the third impedance threshold corresponds to a value equal to or less than 50 kilo ohm.

3. The electrical signal monitoring medical system of claim 1, wherein the processor is further configured to determine a daily activity routine of the person.

4. The electrical signal monitoring medical system of claim 3, wherein the processor is further configured to correlate the determined daily activity routine of the person with a plurality of indications of attachment integrity determined per day.

5. The electrical signal monitoring medical system of claim 1, wherein the processor is configured to determine the indication of attachment integrity based, at least in part, on a number of indications determined over a period of time.

6. The electrical signal monitoring medical system of claim 1, wherein to activate the alert, the processor is configured to activate a visual alert.

7. The electrical signal monitoring medical system of claim 6, wherein to activate the alert, the processor is configured to activate a light emitting diode (LED).

8. The electrical signal monitoring medical system of claim 6, wherein to activate the alert, the processor is configured to activate a display, the display configured to be a user interface.

9. The electrical signal monitoring medical system of claim 1, wherein the processor is further configured to:
- determine a number of intermittent leads-off conditions for a period of time; and
- determine whether the number of intermittent leads-off conditions for the period of time are within a predetermined parameter.

10. The electrical signal monitoring medical system of claim 1, wherein the processor is further configured to utilize one or more combinations of an amount of time the at least one electrode is off, a percentage of time that the at least one electrode is off, and a number of noise events experienced by the at least one electrode to determine the first, the second, and the third impedance thresholds.

11. A method for determining electrode leads off conditions of a medical device, the method comprising:
- determining, by a processor, an impedance at at least one electrode, wherein the determining the impedance corresponds to determining an indication of attachment integrity of the at least one electrode on a skin of a person;
- categorizing the at least one electrode into a category of a plurality of categories based, at least in part, on the determined impedance at the at least one electrode, each of the plurality of categories being associated with the attachment integrity, wherein the categorizing of the at least one electrode comprises:
  - comparing the determined impedance at the at least one electrode with a first impedance threshold to determine a first category of the at least one electrode;
  - comparing the determined impedance at the at least one electrode with a second impedance threshold to determine a second category of the at least one electrode; and
  - comparing the determined impedance at the at least one electrode with a third impedance threshold to determine a third category of the at least one electrode;
- responsive to determining that the determined category of the at least one electrode is the first category, activating a first alert of a plurality of alerts;
- responsive to determining that the determined category of the at least one electrode is the second category, activating a second alert of the plurality of alerts, wherein the second alert is activated slower than the first alert, and wherein an alert is abstained from activating responsive to a determination of the third category of the at least one electrode;

responsive to activating the first or the second alert, causing a corrective action to be performed to restore the attachment integrity of the at least one electrode on the skin;

causing a therapy to be provided to the person to treat a cardiac condition of the person after the corrective action is performed.

12. The method of claim 11, wherein the determining the impedance comprises determining a plurality of changes in impedance.

13. The method of claim 11, wherein the determining the indication of attachment integrity of the at least one electrode comprises determining a plurality of indications per day.

14. The method of claim 11, further comprising determining a daily activity routine of the person.

15. The method of claim 14, wherein the determining the daily activity routine of the person comprises correlating the determined daily activity routine of the person with a plurality of indications of attachment integrity of the at least one electrode determined per day.

16. The method of claim 11, wherein the determining the indication of attachment integrity is based, at least in part, on a number of indications determined over a period of time.

17. The method of claim 11, further comprising:

determining a number of intermittent leads-off conditions for a period of time; and determining whether the number of intermittent leads-off conditions for the period of time are within a predetermined parameter.

18. The method of claim 11, further comprising utilizing one or more combinations of an amount of time the at least one electrode is off, a percentage of time that the at least one electrode is off, and a number of noise events experienced by the at least one electrode to determine the first, the second, and the third impedance thresholds.

19. A method for determining electrode leads off and leads on conditions of a medical device, the method comprising:

determining, by a processor, an impedance at at least one electrode, wherein the determining the impedance corresponds to determining an indication of attachment integrity of the at least one electrode on a skin of a person, and wherein the determining the indication comprises determining a plurality of indications having both leads on and leads off indications of the at least one electrode on the skin over a period of time;

categorizing the at least one electrode into a category of a plurality of categories based, at least in part, on the determined plurality of indications, each of the plurality of categories being associated with the attachment integrity, wherein the categorizing of the at least one electrode comprises:

comparing the determined impedance at the at least one electrode with a first impedance threshold to determine a first category of the at least one electrode categorized as first leads off condition;

comparing the determined impedance at the at least one electrode with a second impedance threshold to determine a second category of the at least one electrode categorized as second leads off condition; and comparing the determined impedance at the at least one electrode with a third impedance threshold value to categorize a third category of the at least one electrode categorized as third leads on condition;

responsive to determining that the category of the at least one electrode is the first category, activating a first alert of a plurality of alerts;

responsive to determining that the category of the at least one electrode is the second category, activating a second alert of the plurality of alerts, wherein the second alert is activated slower than the first alert;

abstaining from activating an alert during the determined third category of the at least one electrode;

responsive to activating the first or the second alert, causing a corrective action to be performed to restore the attachment integrity of the at least one electrode on the skin; and causing a therapy to be provided to the person to treat a cardiac condition of the person after the corrective action is performed.

20. The method of claim 19, wherein the determining the plurality of indications comprises determining whether the leads on and leads off indications are within a percentage of electrode attachment on the skin for a period of time.

21. The method of claim 19, wherein the determining the plurality of indications comprises determining whether the leads on and leads off indications are within a length of time.

22. The method of claim 19, wherein the determining the plurality of indications comprises determining whether the leads off indications are continuous.

23. The method of claim 19, wherein the determining the plurality of indications comprises determining a number of the plurality of indications of attachment integrity.

24. The method of claim 19, further comprising utilizing one or more combinations of an amount of time the at least one electrode is off, a percentage of time that the at least one electrode is off, and a number of noise events experienced by the at least one electrode to determine the first, the second, and the third impedance thresholds.

25. An electrical signal monitoring medical system, comprising:

a plurality of electrodes, the plurality of electrodes configured to be attachable to a skin of a person; and a processor communicatively coupled to the plurality of electrodes, the processor configured to:

determine a plurality of indications of attachment integrity of one or more of the plurality of electrodes on the skin, wherein the plurality of indications are determined by determination of an impedance at the one or more of the plurality of electrodes over a period of time;

categorize the one or more of the plurality of electrodes into a category of a plurality of categories based, at least in part, on the determined impedance at the one or more of the plurality of electrodes, each of the plurality of categories being associated with the attachment integrity, wherein the plurality of categories of the one or more of the plurality of electrodes comprises:

a first category of the one or more of the plurality of electrodes categorized based on the determined impedance at the one or more of the plurality of electrodes with a first impedance threshold;

a second category of the one or more of the plurality of electrodes categorized based on a comparison of the determined impedance at the one or more of the plurality of electrodes with a second impedance threshold; and a third category of the one or more of the plurality of electrodes categorized based on a comparison of the determined impedance at the one or more of the plurality of electrodes with a third impedance threshold;

responsive to a determination that the category of the one or more electrodes is the first category, activate a first alert of a plurality of alerts;

responsive to a determination that the category of the one or more electrodes is the second category, activate a second alert of the plurality of alerts, wherein the second alert is activated slower than the first alert, and wherein the processor is further configured to abstain from activating an alert responsive to a determination of the third category of the one or more of the plurality of electrodes;

responsive to the activation of the first or the second alert, cause a corrective action to be performed to restore the attachment integrity of the at least one electrode on the skin; and cause a therapy to be provided to the person to treat a cardiac condition of the person after the corrective action is performed.

26. The electrical signal monitoring medical system of claim 25, wherein the processor is configured to determine the plurality of indications from a predetermined number of the plurality of electrodes.

27. The electrical signal monitoring medical system of claim 25, wherein the processor is further configured to utilize one or more combinations of an amount of time the one or more of the plurality of electrodes are off, a percentage of time that the one or more of the plurality of electrodes are off, and a number of noise events experienced by the one or more of the plurality of electrodes to determine the first, the second, and the third impedance thresholds.

28. An electrical signal monitoring medical system, comprising:

a plurality of electrodes, the plurality of electrodes configured to be attachable to a skin of a person;

a processor communicatively coupled to the plurality of electrodes, the processor configured to:

determine one or more indications of attachment integrity of the plurality of electrodes on the skin, wherein the one or more indications are determined by determination of an impedance at each of the plurality of electrodes over a period of time;

categorize each of the plurality of electrodes into a category of a plurality of categories based, at least in part, on the determined impedance at each of the plurality of electrodes, each of the plurality of categories being associated with the attachment integrity, wherein the plurality of categories of each of the plurality of electrodes comprises:

a first category of respective electrode of the plurality of electrodes categorized based on the determined impedance at the respective electrode with a first impedance threshold; and a second category of respective electrode of the plurality of electrodes categorized based on the determined impedance at the respective electrode with a second impedance threshold;

responsive to a determination that the category of the respective electrode of the plurality of electrodes is the first category, activate a first alert of a plurality of alerts;

responsive to a determination that the category of the respective electrode of the plurality of electrodes is the second category, activate a second alert of the plurality of alerts, wherein the second alert is activated slower than the first alert;

responsive to the activation of the first or the second alert, cause a corrective action to be performed to restore the attachment integrity of the at least one electrode on the skin; and cause a therapy to be provided to the person to treat a cardiac condition of the person after the corrective action is performed.

* * * * *